(12) United States Patent
Tumer et al.

(10) Patent No.: US 7,818,047 B2
(45) Date of Patent: Oct. 19, 2010

(54) X-RAY AND GAMMA RAY DETECTOR READOUT SYSTEM

(75) Inventors: Tumay O Tumer, Riverside, CA (US); Martin Clajus, Los Angeles, CA (US); Gerard Visser, Bloomington, IN (US)

(73) Assignee: Nova R&D, Inc., Riverside, CA (US)

( * ) Notice: Subject to any disclaimer, the term of this patent is extended or adjusted under 35 U.S.C. 154(b) by 2445 days.

(21) Appl. No.: 10/291,251

(22) Filed: Nov. 8, 2002

(65) Prior Publication Data
US 2003/0105397 A1 Jun. 5, 2003

Related U.S. Application Data

(60) Provisional application No. 60/331,161, filed on Nov. 9, 2001.

(51) Int. Cl.
*A61B 6/00* (2006.01)
(52) U.S. Cl. ............ 600/436; 250/370.09; 250/363.03; 250/368; 250/367; 250/369
(58) Field of Classification Search ............ 250/370.09, 250/363.03, 368, 367, 369; 600/436
See application file for complete search history.

(56) References Cited

U.S. PATENT DOCUMENTS

| | | | | |
|---|---|---|---|---|
| 4,864,140 A | * | 9/1989 | Rogers et al. | 250/369 |
| 5,138,165 A | * | 8/1992 | Petroff | 250/363.03 |
| 5,396,187 A | * | 3/1995 | Binkley | 327/552 |
| 5,451,789 A | * | 9/1995 | Wong et al. | 250/363.03 |
| 5,719,400 A | * | 2/1998 | Cherry et al. | 250/368 |
| 5,786,597 A | * | 7/1998 | Lingren et al. | 250/370.09 |

(Continued)

OTHER PUBLICATIONS

Kravis, Scott D., et al., "Test Results of the Readout Electronics for Nuclear Applications (RENA) Chip Developed for Position-Sensitive Solid State Detectors," SPIE (Society of Photo-Optical Instrumentation Engineers), vol. 3445, Jul. 1998, pp. 374-382.

(Continued)

*Primary Examiner*—Brian Casler
*Assistant Examiner*—John F Ramirez
(74) *Attorney, Agent, or Firm*—Fish & Associates, PC

(57) ABSTRACT

A readout electronics scheme is under development for high resolution, compact PET (positron emission tomography) imagers based on LSO (lutetium ortho-oxysilicate, $Lu_2SiO_5$) scintillator and avalanche photodiode (APD) arrays. The key is to obtain sufficient timing and energy resolution at a low power level, less than about 30 mW per channel, including all required functions. To this end, a simple leading edge level crossing discriminator is used, in combination with a transimpedance preamplifier. The APD used has a gain of order 1,000, and an output noise current of several $pA/\sqrt{Hz}$, allowing bipolar technology to be used instead of CMOS, for increased speed and power efficiency. A prototype of the preamplifier and discriminator has been constructed, achieving timing resolution of 1.5 ns FWHM, 2.7 ns full width at one tenth maximum, relative to an LSO/PMT detector, and an energy resolution of 13.6% FWHM at 511 keV, while operating at a power level of 22 mW per channel. Work is in progress towards integration of this preamplifier and discriminator with appropriate coincidence logic and amplitude measurement circuits in an ASIC suitable for a high resolution compact PET instrument. The detector system and/or ASIC can also be used for many other applications for medical to industrial imaging.

24 Claims, 27 Drawing Sheets

U.S. PATENT DOCUMENTS 5,821,541 A * 10/1998 Tumer .................. 250/370.09

OTHER PUBLICATIONS

Kravis, Scott D., et. al., "A multichannel readout electronics for nuclear applitation RENA) chip developed for position sensitive solid state detectors," *Nuclear Instruments & Methods in Physics Research*, A 422, 1999, pp. 352-356.

Mainprize, James G., et al., "Image Quality of a Prototype Direct Conversion Detector for Digital Mammography," *Society of Photo-Optical Instrumentation Engineers*, 1999.

He, Z., et al., "3-D position sensitive CdZnTe gamma-ray spectrometers," *Nuclear Instruments & Methods in Physics Research*, A 422, 1999, pp. 173-178.

Matteson, James L., "Position-sensitive CZT detector module," *SPIE* (Society of Photo-Optical Instrumentation Engineers), vol. 3446, Jul. 1998, pp. 192-201.

Yasillo, Nicholas J., et al., "Design Considerations for a Single Tube Gamma Camera," *IEEE Transactions on Nuclear Science*, vol. 37, No. 2, Apr. 1990, pp. 609-615.

Bird, A.J., et al., "Images obtained with a compact gamma camera," *Nuclear Instruments & Methods in Physics Research*, A 499, 1990, pp. 480-483.

Holl, P., et al., "A Double-sided Silicon Strip Detector with Capacitive Readout and a New Method of Integrated Bias Coupling," *IEEE Transactions on Nuclear Science*, vol. 36, No. 1, Feb. 1989, pp. 251-255.

Hall, G., "Silicon Drift Chambers," *Nuclear Instruments & Methods in Physics Research*, A 273, 1988, pp. 559-564.

Aarsvold, J.N. et al., "Modular scintillation cameras: a progress report," *SPIE* (Society of Photo-Optical Instrumentation Engineers), vol. 914, Medical Imaging II, 1988, pp. 319-325.

* cited by examiner

X-RAY AND GAMMA RAY DETECTOR READOUT SYSTEM

CROSS REFERENCE TO PROVISIONAL PATENT APPLICATION

This application claims the benefit of the filing date of U.S. Provisional Patent Application No. 60/331,161 filed Nov. 9, 2001, the disclosure of which is incorporated herein by reference.

GOVERNMENT RIGHTS NOTICE

There invention was made with U.S. Government support under Contract Numbers DE-FG03-00ER83058 and DE-FG03-00ER83058/A002, both awarded by Department of Energy. The U.S. Government has certain rights in the invention.

FIELD OF INVENTION

These detectors and readout electronics have been developed for high resolution Positron Emission Tomography (PET) for application to medical imaging. PET is an important new modality for imaging metabolism of organic radiopharmaceuticals and radiotracers. The detector system described here can also be used for non-tomographic medical imaging of positron emitting compounds. It can also be used for other gamma ray imaging medical applications such as Gamma Camera and Single Photon Emission Computed Tomography (SPECT).

The instrument described can also be used for many different applications. In industrial imaging, for example, they can be used for different gamma ray imaging applications such as Non-Destructive Inspection (NDI) and Non-Destructive Evaluation (NDE). In NDI and NDE it can be used to image objects for defects, bubbles, cracks, etc. It may also be used to detect corrosion and cracks on aircraft and other vehicles. In security applications it can be used to scan baggage, parcel, container and vehicle. It can also be used to scan people and search for radioactive material. In military it can be used in the field in a different portable embodiment to search and image radioactive material and/or objects that contain radioactive materials.

The Application Specific Integrated Circuit (ASIC) is being developed can be also used for other applications. It may be used for astrophysics and nuclear physics. It may become an important readout chip for instruments, which use Compton Scatter technique to image gamma rays. The ASIC may also have other Applications for medical and industrial imaging markets.

BACKGROUND OF INVENTION

The American Cancer Society estimates more than 180,000 new breast cancer diagnoses and more than 40,000 deaths from breast cancer in the United States in about one year. Mammography is a useful screening tool for detecting breast cancer, reducing mortality by about 25%, but is limited by a large number of false positive tests resulting in unnecessary biopsies and, more importantly, a considerable number of false negative tests resulting in missed diagnosis of cancer. In the last few years it has become apparent that nuclear medicine techniques have the potential to play an important role in the diagnosis and treatment of patients with breast cancer. Positron emission tomography (PET), using [$^{18}$F]fluoro-2-deoxy-D-glucose (FDG) as a tracer of tumor glucose metabolic activity, is an accurate, non-invasive imaging technology, which probes tissue and organ function. This provides information, which is complementary to the structural image obtained from mammography. Whole body PET is a well established technology, however it is expensive, and of limited availability. Furthermore, the spatial resolution is 8-16 mm, insufficient for accurate detection and imaging of smaller tumors. The extension of PET to small, more widely available, higher spatial resolution (<3 mm) systems optimized for breast cancer imaging has the potential to save many lives. Therefore, we have designed this PET system for dedicated breast imaging. However, it can be used for full body PET and has many other uses as described above, in section on Field of Invention.

For the reasons of cost and availability it is unrealistic to expect nuclear medicine techniques to be used for mass screening. There are, however, several important situations in which the results from mammography can be unsatisfactory, and the availability of a functional imaging technique to provide additional diagnostic information would be extremely helpful. These situations include:

1. Imaging of young women with very dense breasts (where mammograms are often of poor quality and the detection of early stage breast cancer is difficult and inaccurate).
2. Imaging in women with silicone breast implants (these have high radiodensity and breast displacement is not always possible or effective).
3. Imaging in women with widespread fibrocystic changes.
4. Screening for post-lumpectomy tumor recurrence—the number of women opting for breast conservation is increasing, and functional imaging techniques, particularly the use of FDG with PET, have been shown to be extremely good at differentiating recurrent tumor from scar tissue or radiation necrosis.

Encouraging preliminary studies have already been carried out using [$^{99m}$Tc]sestamibi with conventional gamma cameras and 2-[$^{18}$F]-fluoro-2-deoxy-D-glucose (FDG) with whole-body PET scanners. The role of functional imaging in breast cancer, however, goes far beyond diagnosis. It is possible that PET techniques could become fundamental in predicting and monitoring the effectiveness of therapy, in particular chemotherapy and hormonal therapy. Metabolic activity as measured by FDG PET has been shown to be a more sensitive indicator of tumor response than anatomical techniques. This would allow early response to treatment to be identified and the chemotherapeutic regimen altered in the absence of a response. In addition, PET can be used to assess the concentration of estrogen receptors using the estrogen derivative [$^{18}$F]fluoroestradiol. The concentration of estrogen receptors is an important predictor of the outcome of hormonal therapy.

In the future, chemotherapeutic agents could be directly labeled with positron emitters and given in trace amounts to predict response prior to the use of pharmacological levels. This might allow tailoring of the drug regimen to the individual patient, leading to a reduction in the costs and morbidity of ineffective treatments. Further interesting possibilities involve labeling monoclonal antibodies directed against breast tumor cells with $^{124}$I. This long-lived tracer would allow the distribution of antibodies to be visualized prior to therapy

SUMMARY OF INVENTION

Mammography allows the detection of very small, non-palpable lesions and has become the screening modality of choice in postmenopausal women. However, this technique has a limited diagnostic accuracy for detecting cancer, and image interpretation is subject to considerable inter- and intra-observer variability. Its sensitivity drops considerably in women with dense, fibrocystic breasts. The incidence of positive biopsies performed after mammographic findings ranges from 9% to 65%, with most investigators reporting a 15 to 30% positive biopsy rate. Microcalcifications, one of the classic signs of occult malignancies, have a low predictive value of only 11.5% for the presence of cancer. The predictive value of masses that are thought to definitely represent malignancies is about 74%, but masses thought to be possibly malignant turn out to be carcinoma in only 5.4% of the cases. Several studies have reported substantial variability among radiologists in interpretation of mammographic examinations. Observer agreement was two-times more likely for examinations with less dense breasts. Other factors such as age, ethnicity and estrogen replacement status affect mammographic sensitivity. Sensitivity was only 54% in women younger than 40 years and 68% in women with dense breasts (vs. 85% for non-dense breasts). In summary, mammography is a useful screening tool for detecting cancer but is limited by a large number of false positive tests resulting in unnecessary biopsies and, more importantly, a considerable number of false negative tests resulting in missed diagnosis of cancer, which results in unnecessary deaths. It will be important if false negatives can be significantly reduced to save lives.

In the last few years it has become apparent that nuclear medicine techniques have the potential to play an important role in the diagnosis and management of patients with breast cancer. Positron Emission Tomography (PET), using [$^{18}$F] fluoro-2-deoxy-D-glucose (FDG) as a tracer of tumor glucose metabolic activity, is an accurate, non-invasive imaging technology, which probes tissue and organ function. This provides information, which is complementary to the structural image obtained from mammography. Whole body PET is used clinically to diagnose and stage a variety of cancers. It detects breast cancer with sensitivities between 70 and 90% and specificities of 84-97%. The somewhat lower than desired sensitivity is due to relatively poor accuracy for detecting tumors of less than 1 cm in size. A high diagnostic accuracy of PET imaging for staging of axillary lymph node involvement has also been reported. The detection of malignant breast tumors with PET is limited by the spatial resolution and sensitivity of whole body PET systems. State-of-the-art whole body PET systems typically yield reconstructed images with a resolution of 8-16 mm depending on the injected dose, imaging time, and intrinsic resolution of the scanner. Whole body PET is also an expensive technology, which is generally only available in the larger medical facilities in the U.S. Therefore, a dedicated compact higher resolution PET system that improves the sensitivity, specificity, and availability of PET imaging for breast cancer detection, which can also be used for many other applications is discussed below.

A highly integrated multichannel mixed-signal (both analog and digital) front-end electronics for the LSO-based PET (positron-emission tomography) imager is developed. The LSO (lutetium ortho-oxysilicate, $Lu_2SiO_5$) scintillator crystals are read out at both ends by avalanche photodiodes (APDs) supplied by RMD Inc. (Watertown, Mass.). Innovative front-end electronics is essential for the development of commercial PET systems. The small scintillator area (2×2 $mm^2$) leads to a large number of channels (in the range of 5,000-20,000) and requires high-density electronics. Therefore, multichannel front-end electronics integrated into a mixed signal ASIC (Application Specific Integrated Circuit) is essential to build a compact PET imager based on APD array readout. We have designed an innovative, fast, low-noise multichannel mixed signal ASIC for the LSO/APD arrays for application to breast cancer diagnosis. The development of such an ASIC involves many challenges due to its charge-sensitive nature and multichannel design, including crosstalk, electromagnetic pickup, feedback from digital sections into the highly sensitive front end, and fast trigger output for the tight PET coincidence requirement. Innovation also includes the development of highly compact readout electronics so that the PET instrument as a whole will be compact. The approach of placing APD arrays on both front and back sides of the LSO crystals is also an innovative concept that poses design challenges in ensuring that the amount of absorber material in the photons' path is kept to a minimum.

Several design options have been investigated and a preliminary design for the ASIC is developed with particular emphasis on the preamplifier and discriminator sections, which we consider the most critical components for the project's success. The design is based on the performance requirements identified for the PET imager in general and the readout electronics in particular. Specifically, good timing resolution on the order of 3 ns or better and low power consumption are critical for the practical usefulness of the PET imager that will result from this project. By building a transistor-level prototype of the critical components of the circuit—the preamplifier and the discriminator—and demonstrating that it meets or even exceeds the design goals set forth in our project, the ASIC circuit is tested and verified.

An ASIC-based readout electronics scheme is designed for high resolution, compact PET imagers based on independent readout of all channels of LSO scintillator and avalanche photodiode (APD) arrays. Depth of interaction is obtained by readout of both ends of the LSO crystals. A low power, highly integrated design is critical. We report here on a discrete electronics prototype, running at 22 mW per channel for the preamplifier and discriminator. The measured timing resolution is 3.6 ns FWHM, 9.2 ns full width at one tenth maximum, relative to an LSO/PMT detector, energy resolution is 13.3% FWHM at 511 keV, and depth of interaction position resolution is 2.5 mm FWHM throughout the full length of the crystal.

The preliminary ASIC design is completed by adding other required circuitry, such as a shaper and peak detector and trigger logic. The ASIC is instrumental in building two LSO/APD modules, each consisting of a 4×4 crystal array read out at both ends. The module is designed to achieve a full-fledged, commercially viable breast cancer PET detector system.

Detector modules based on recently developed planar-processed avalanche photodiode (APD) arrays from RMD (Radiation Monitoring Devices, Inc.) and LSO scintillator crystals are used. The APD arrays are available with a 2.48 mm or a 1.27 mm pitch from RMD (Radiation Monitoring Devices, Inc.); the 2.48 mm pitch array, which we work with here has a pixel active area of 2×2 $mm^2$, a gain of order 1,000, and capacitance of 2.8 pF (excluding packaging). For room temperature operation, the leakage current is around 100 nA and the current noise is several pA/$\sqrt{Hz}$, when operated near maximum gain (for optimal timing resolution). The quantum efficiency is >60% at 420 nm, the peak emission wavelength of LSO. Our early measurements have been performed with a single channel APD of the same 2×2 $mm^2$ geometry and the same specifications.

The compact geometry and low mass of the APD arrays allow for double-ended readout of the LSO crystals, to make depth of interaction (DOI) measurements, with the added engineering advantage of identical readout electronics for both sides of the crystal array. DOI measurement is critical to achieving a uniform spatial resolution in combination with high efficiency in an affordable instrument, with a ring diameter of about 20 cm. Another advantage of APDs is their relative insensitivity to magnetic fields, possibly enabling co-imaging with PET and NMR techniques in the future.

A complete, highly integrated, low power readout electronics chain optimized for high resolution APD/LSO PET imaging is to date not available, although encouraging results have been reported for individual circuit blocks such as the preamplifier and discriminator. A high resolution PET scanner with DOI for breast cancer imaging will involve 5,000-20,000 channels, making power dissipation a very critical parameter. Position sensitive readout schemes (charge division) can be used to reduce the number of electronics channels, but bring in additional uncertainty in the position measurement and increase the electronics channel hit rate, requiring lower dead time. Since the avalanche gain in an APD is relatively low (compared to a typical PMT (photomultiplier tube)), sophisticated low noise electronics must be placed in close proximity to the APDs, further complicating the power dissipation issue.

For minimum system power dissipation, a leading edge level crossing discriminator is used, carefully designed to minimize time walk. For pulses with amplitude greater than about 50% of the photopeak, the time walk can be controlled within 1-2 ns. However, the leading edge of the LSO scintillation light must be observed with the maximum possible bandwidth. A high speed transimpedance preamplifier is used, preserving the bandwidth of the APD. In contrast to the case of a charge sensitive preamplifier, no fast shaper or complex discriminator is required in the timing path, offering considerable power savings. Furthermore, pole/zero cancellation is irrelevant for a transimpedance preamplifier, an important advantage for high rate operation. The pulse amplitude measurement proceeds by using a low power slow shaper and peak stretcher followed by an A/D converter.

The APD output in response to a typical 511 keV LSO scintillation pulse is shown in FIG. 12. The APD bias is 1,824 V, the crystal dimensions are 2×2×10 mm$^3$, and the measurement bandwidth is 240 MHz. The fit 10%-90% risetime is 10 ns, so allowing a 2 ns degradation the transimpedance amplifier bandwidth should be set around 53 MHz. The APD risetime is limited by diffusion of electrons in the low field region above the gain region.

DESCRIPTION OF THE PREFERRED EMBODIMENTS

Figure 1:
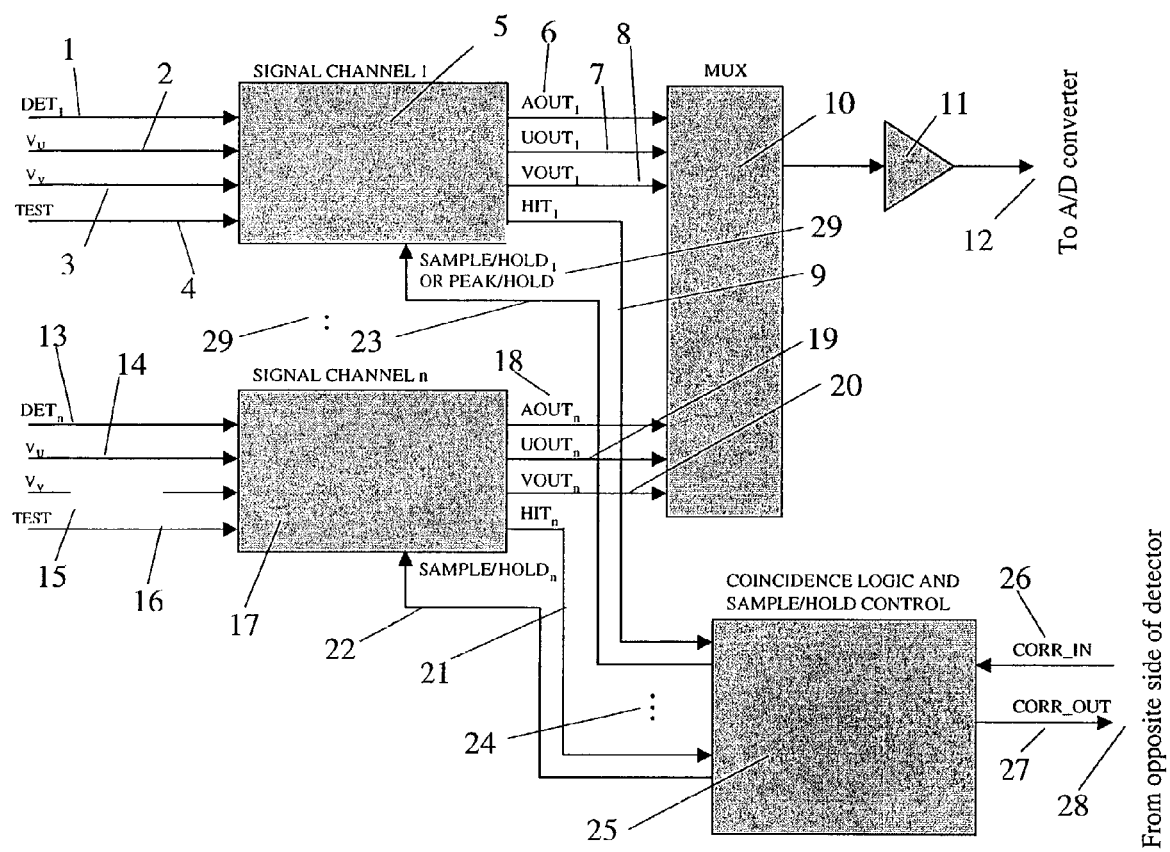
FIG. 1 is an overall block diagram of the LSO/APD PET Imaging ASIC.

There has been considerable interest in recent years in developing dedicated high resolution positron emission tomography (PET) systems for applications in breast cancer imaging and small-animal imaging. The goal in these systems is to achieve much higher spatial resolution and sensitivity for specific tasks than is possible with whole-body PET scanners designed for general purpose use. A second goal is to produce relatively inexpensive, compact and easy to use systems that make PET more accessible. Generally, these dedicated systems use small scintillator elements read out by position-sensitive or multi-channel PMTs. In most systems, some form of signal multiplexing is used to reduce the number of channels to a manageable number. Since the predominant mode of interaction at 511 keV in all scintillators currently used for PET is Compton scatter, multiplexing can lead to significant loss of position information. Furthermore, depth-of-interaction (DOI) blurring or radial elongation error becomes a prominent feature in these small diameter systems, and therefore several groups have been exploring detector approaches that can measure DOI.

Recently, avalanche photodiode (APD) arrays have become available that when combined with $Lu_2SiO_5$ (LSO) scintillator crystals offer new opportunities for high resolution PET detectors. This work focuses on the high-gain APD arrays developed by RMD, Inc. (Watertown, Mass.). The APD arrays are available with a 2.48 mm (16 channels) or a 1.27 mm pitch (64 channels); the 2.48 mm pitch array, which we work with here has a pixel active area of 2 mm×2 mm, a gain of order 1,000, and capacitance per pixel of 2.8 pF. For room temperature operation, the leakage current is around 100 nA and the current noise is around 5 pA/√Hz, when operated near maximum gain (for optimal timing resolution). The quantum efficiency is greater than 60% at 420 nm, the peak emission wavelength of LSO. The work reported here has been performed with a single channel APD of the same 2 mm×2 mm geometry and the same specifications.

The compact geometry and low mass of the APD arrays allow for double-ended readout of the LSO crystals, to make DOI measurements, with the added engineering advantage of identical readout electronics for both sides of the crystal array. DOI measurement is critical to achieving uniformly high spatial resolution in combination with high sensitivity in an affordable instrument, with a ring diameter of about 20 cm. Furthermore, the use of completely independent readout channels for each crystal of the array, instead of a position sensitive readout scheme, may enable the accurate analysis, or the unambiguous rejection, of some events involving Compton interactions in the scintillator array. Overall system deadtime can also be significantly reduced by using independent readout channels for each crystal of the array.

Individual readout of each crystal of the array places a high premium on cost, power dissipation, and size and mass of the readout electronics. Most readout functions, including all functions required on a per-channel basis, will have to be integrated into an ASIC before such a system becomes viable. A complete, highly integrated, low power readout ASIC optimized for high resolution PET imaging with LSO/APD arrays is to date not available, although encouraging results have been reported for individual circuit blocks such as the preamplifier and discriminator. We developed such readout electronics, specifically, optimized to meet the crystal identification, timing, energy, and DOI requirements of high resolution PET while minimizing system complexity and cost. The results, confirming that the architecture and specifications of our readout electronics will deliver the performance required for high resolution PET, are presented here.

The APD gain is sufficiently high that the principal electronics noise contribution in the system is the current noise of the APD itself. Therefore, we use a transimpedance amplifier input stage instead of a charge sensitive amplifier. The design minimizes power while preserving the relatively short (5 to 10 ns) risetime of the LSO/APD signal. Since the APD capacitance is only about 2.8 pF, the transimpedance amplifier can have a wide bandwidth with still relatively small noise contributions from the voltage noise of the open loop amplifier and the current noise of the feedback resistor.

For the timing pick-off, a leading edge discriminator is used. This will lead to time walk, although—since the system noise is low enough to allow a threshold around 50 keV or less—the time walk for energies relevant to PET is under control. The long crystals, with surfaces optimized for DOI measurement, add the complication that the pulse height, even for the photopeak, may be small for one of the APDs; to cope with this, we take the time pick-off from either the front or back APD, whichever is the first to cross threshold.

For the pulse height measurement a two-pole low pass filter to shape the pulses with a peaking time of 180 ns, and capture the pulse height in a sample and hold circuit timed from the discriminator output is used. The pulse height is then digitized by a 12-bit successive-approximation A/D converter. (The ASIC will also include a sparse readout circuit to read the pulse height from the front and back APDs of all and only those LSO crystals which are over threshold for a given event.)

The developed system was studied for depth of interaction, energy, and timing resolution. For all of these measurements the APD bias voltages were 1,752.3 V and 1,737.3 V, with absolute accuracy±1.5%; stability and peak-to-peak noise is less than 100 mV. The bias voltages were tuned for the maximum reasonable gain, beyond which the preamplifier output showed a significantly increased noise level. The average photopeak pulse amplitudes seen from the two APDs were within a factor of two of one another. The measured temperature was 30° C., but no active temperature control system was used.

The discriminator thresholds were set at 177 nA and 99 nA, respectively. Pulses from the 511 keV photopeak signal have an amplitude around 1.9 μA, by comparison, so that in energy terms the timing threshold is set less than 47 keV.

The LSO crystal 102 dimensions were 2 mm×2 mm×20 mm; the long faces were plain saw-cut surfaces and both 2 mm×2 mm end faces were mechanically polished. The crystal was wrapped in white teflon tape and coupled to the APDs with a small amount of Bicron BC-630 optical grease.

The second detector 120 for all our measurements was composed of a polished 2 mm×2 mm×10 mm LSO crystal, coupled end-on to a Hamamatsu R1635 PMT 104, 124. A leading edge discriminator 45 (constructed from a Motorola MC100LVEL16 integrated circuit) was used for timing from the PMT.

For the DOI tests, a 3.21 MBq $^{22}$Na source 103, 122 (diameter 1 mm) was placed at a distance of 48 mm perpendicularly from the side of the LSO crystal. The LSO/PMT detector was placed at a distance of 72 mm on the far side of the source. Thus in coincidence a spot size of order of 1.4 mm FWHM is illuminated on the 2 mm×2 mm×20 mm LSO crystal 102, ignoring the effects of the positron range and momentum. The PMT and the source are fixed to a linear motion table parallel to the 2 mm×2 mm×20 mm LSO crystal 102. The position of the motion table, and hence of the illuminated spot on the LSO crystal, is labeled here by the coordinate 'z'. No absolute position calibration was used; z=0 mm is arbitrary, though it is near the back end of the crystal. We recorded 5,000 events at each z position from z=0 mm to 21 mm by steps of 1 mm.

Figure 18:
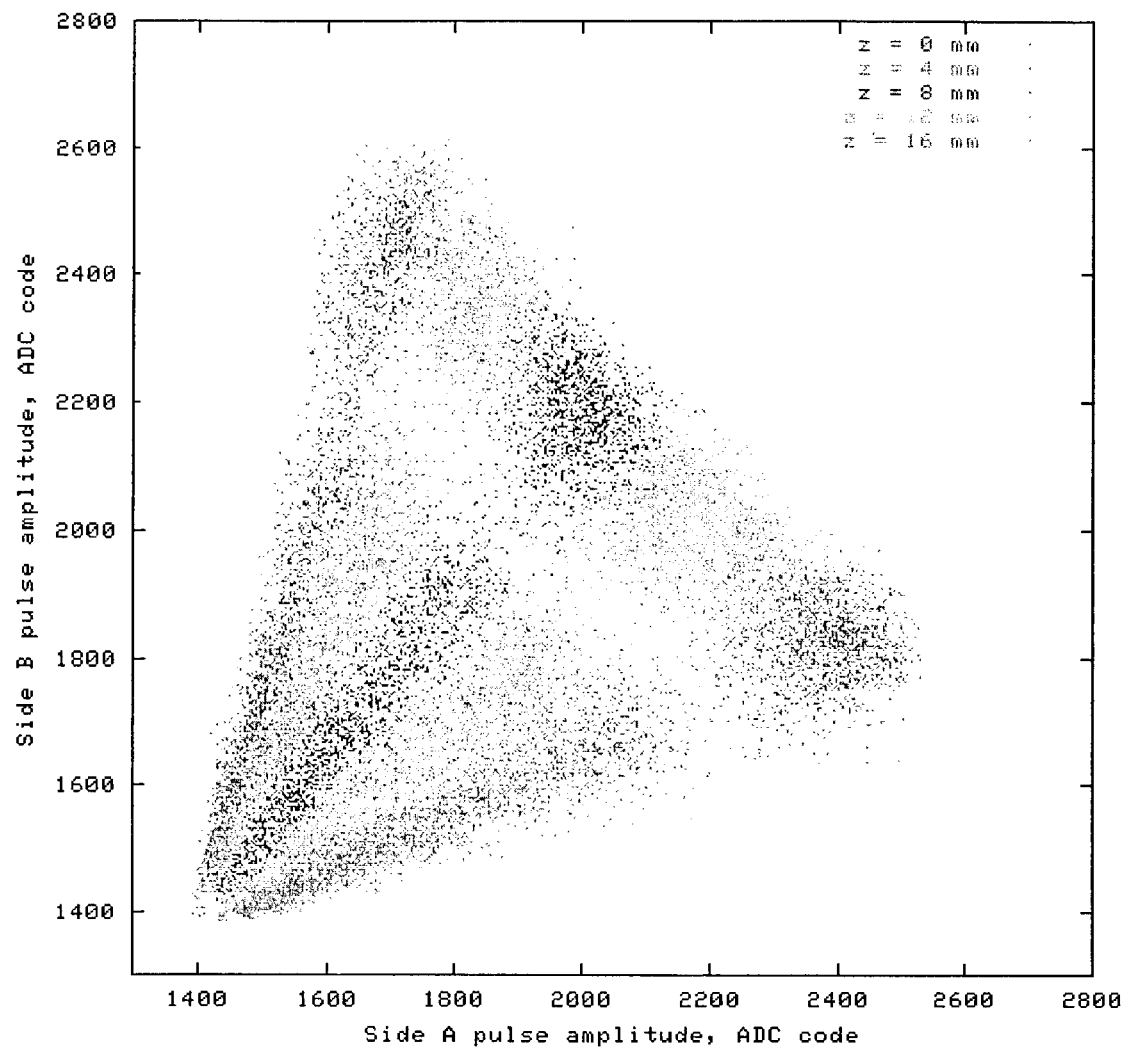
FIG. 18 is a graph of a DOI measurement: Front vs. back pulse height scatter plot, aggregate of five different z positions (0 mm, 4 mm, 8 mm, 12 mm, 16 mm). An approximate energy cut at 250 keV used in some of the analysis (F/620+B/525>1) is equivalent to a line from 750 (vertical scale to 600 (horizontal) scale.

DOI measurement proceeds by a comparison of the scintillation light detected at the front and back ends of the crystal. FIG. 18 shows a scatter plot of pulse height measured on the front APD (F) vs. pulse height measured on the back APD (B), with the source located successively at four different z positions separated by 6 mm. The energy and DOI capability can be quickly appreciated from a consideration of this plot. The baseline level digitized from the A/D converter with zero pulse input has been subtracted from this data (and similarly for the remainder of this paper). No other corrections have been applied to the pulse height data as measured by the A/D converter.

Figure 19:
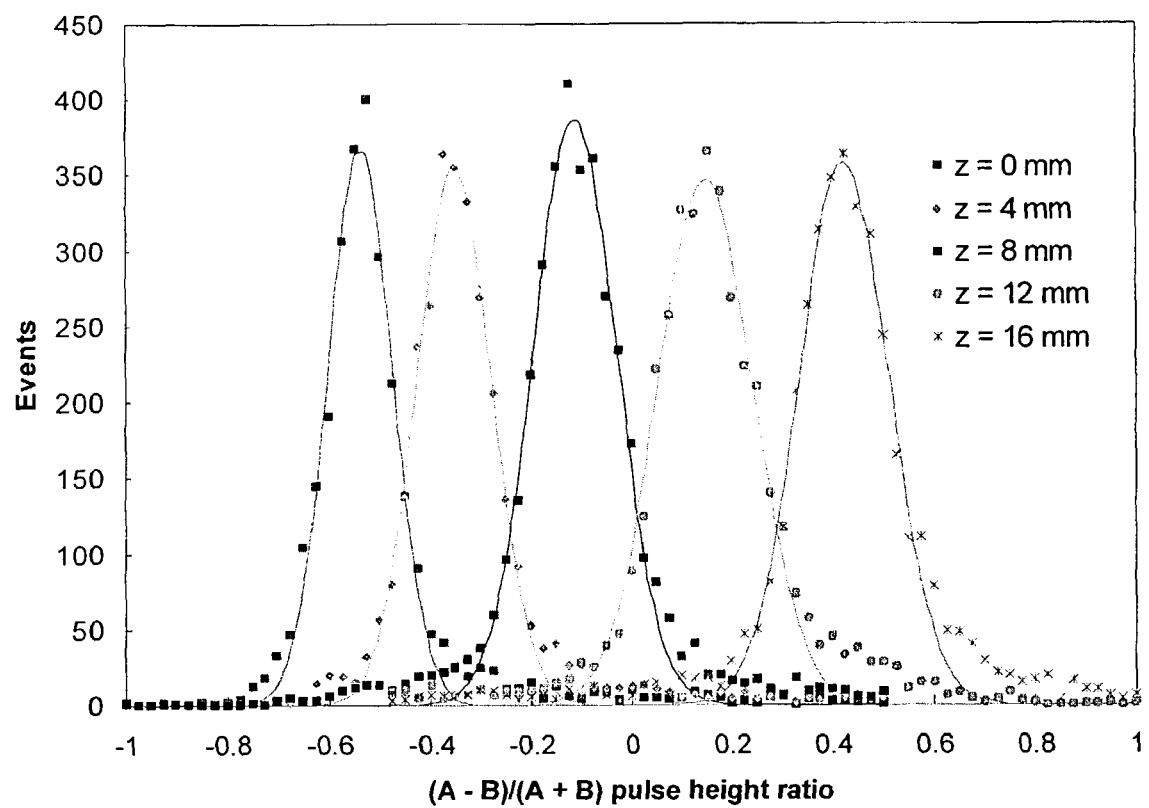
FIG. 19 is a graph of a DOI measurement: pulse height ratio (A−B)/(A+B).

For events at a given z position, the ratio of the front APD pulse height to back APD pulse height is expected to be a constant, and ideally there is a one-to-one correspondence between z and the ratio F/B. It is convenient to use the ratio F/(F+B), or the angle arctan (F/B), for analysis instead of the ratio F/B. FIG. 19 shows histograms of the angle determined from the front to back pulse height ratio, (F−B)/(F+B). Or it is possible to use the direct ratio F/B.

DOI resolution is degraded for low-energy events, where the angular separation in the front vs. back scatter plot evidently is not as great. Typically, however, lower energy thresholds of between 250 and 350 keV are used in a PET system. We therefore also explore the effect of an energy cut (can be represented as a line from 750 (vertical scale) to 600 (horizontal) scale on FIG. 18 for 250 keV cut) on the DOI resolution. Since the DOI resolution shown here is good, it will be important to increase the crystal length beyond 20 mm, which will boost the detection efficiency further.

Figure 20:
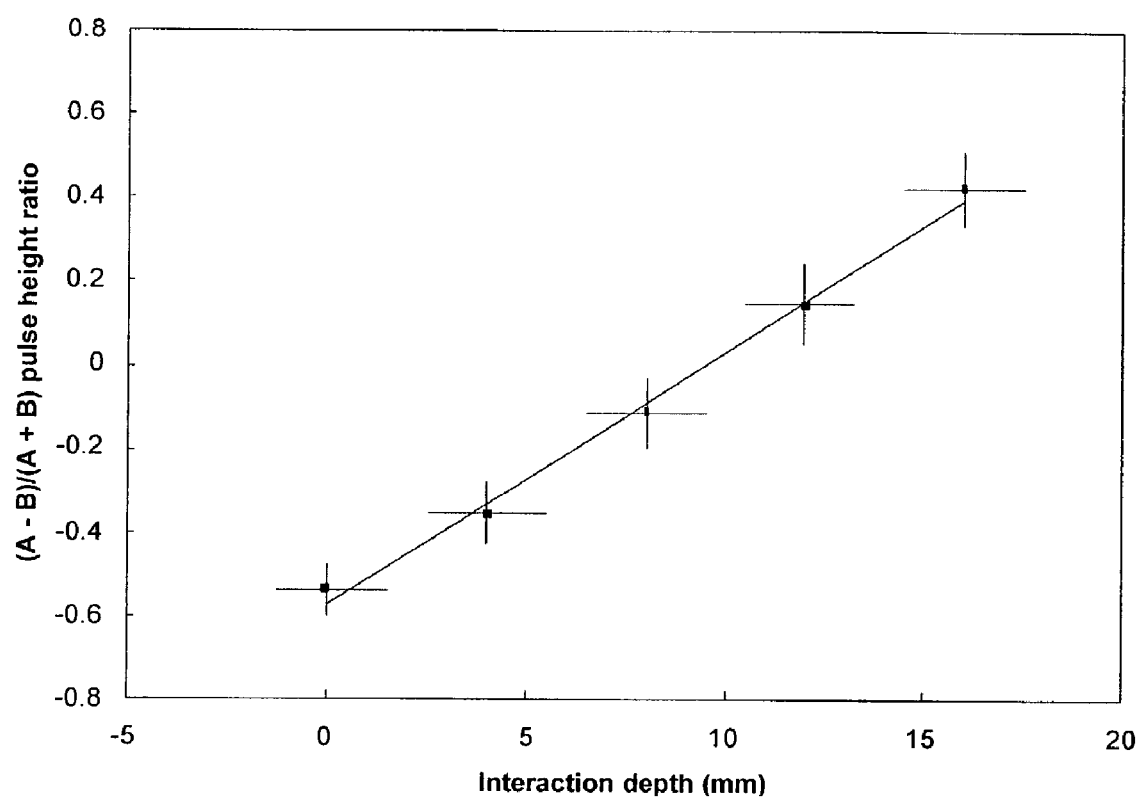
FIG. 20 is a graph of DOI calculated by the pulse height ratio (A−B)/(A+B).
Figure 21:
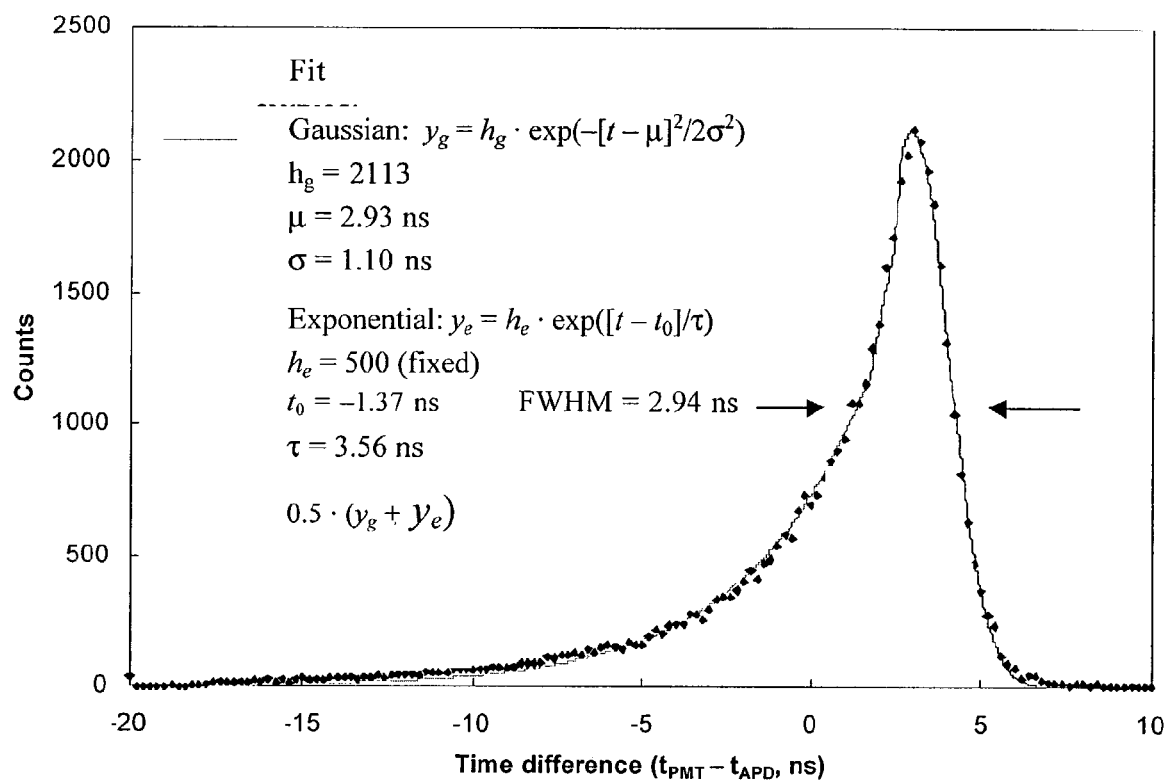
FIG. 21 is a graph of timing differences measured between APD and PMT; APD vs. PMT, no energy cut.
Figure 22:
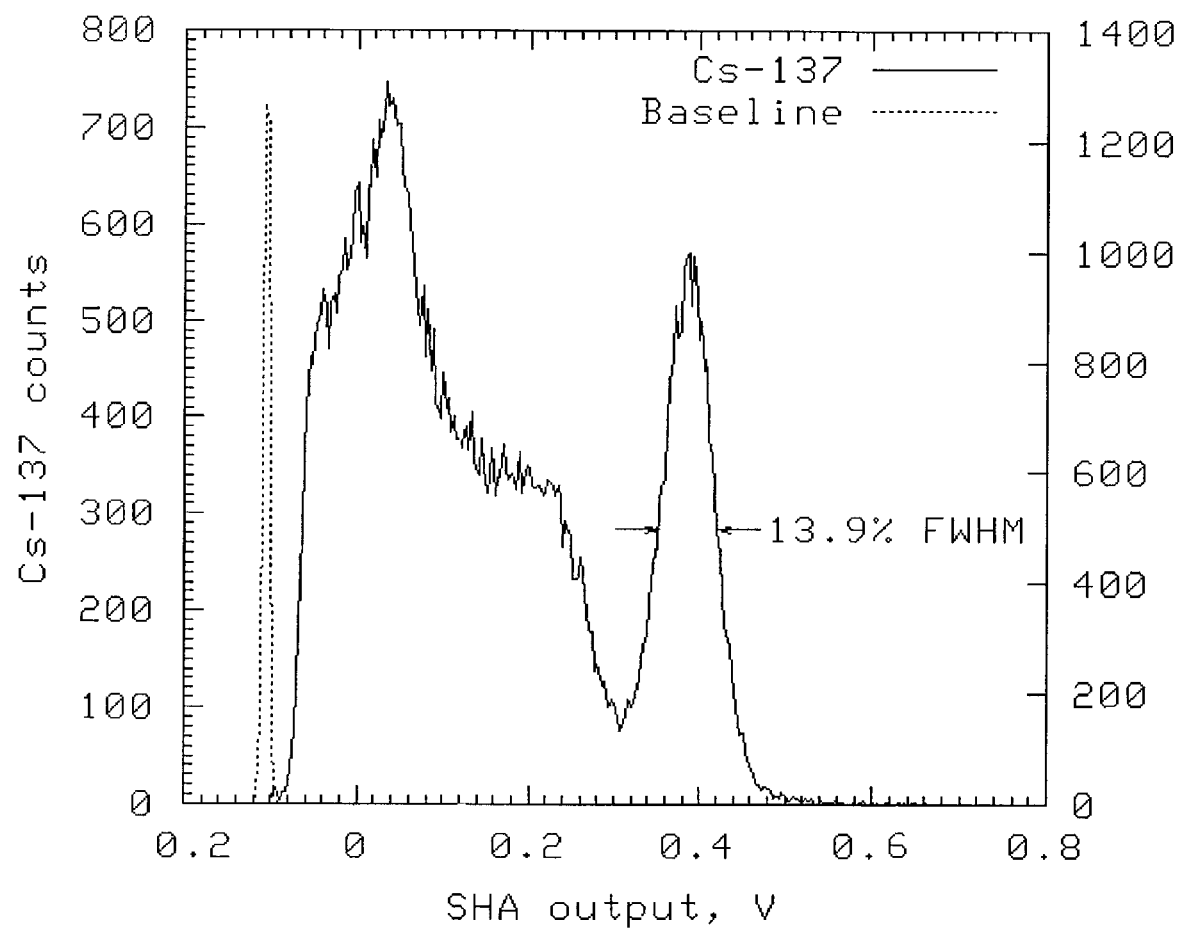
FIG. 22 is a spectrum of $^{137}$Cs using a 2×2×10 mm LSO crystal with single side readout.
Figure 23:
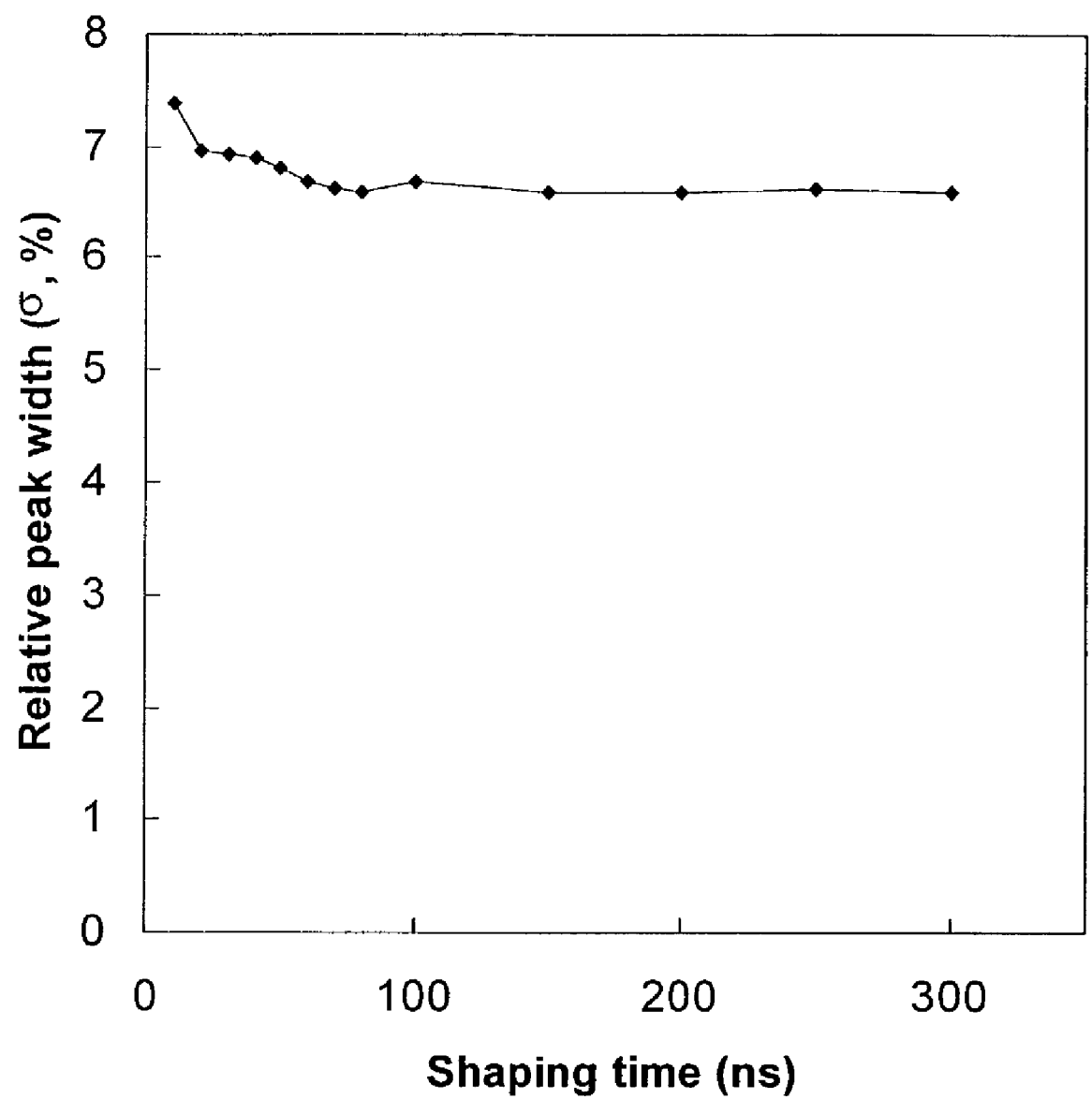
FIG. 23 is a graph of energy resolution at 662 keV as a function of shaping time (signals were peak-detected).
Figure 24:
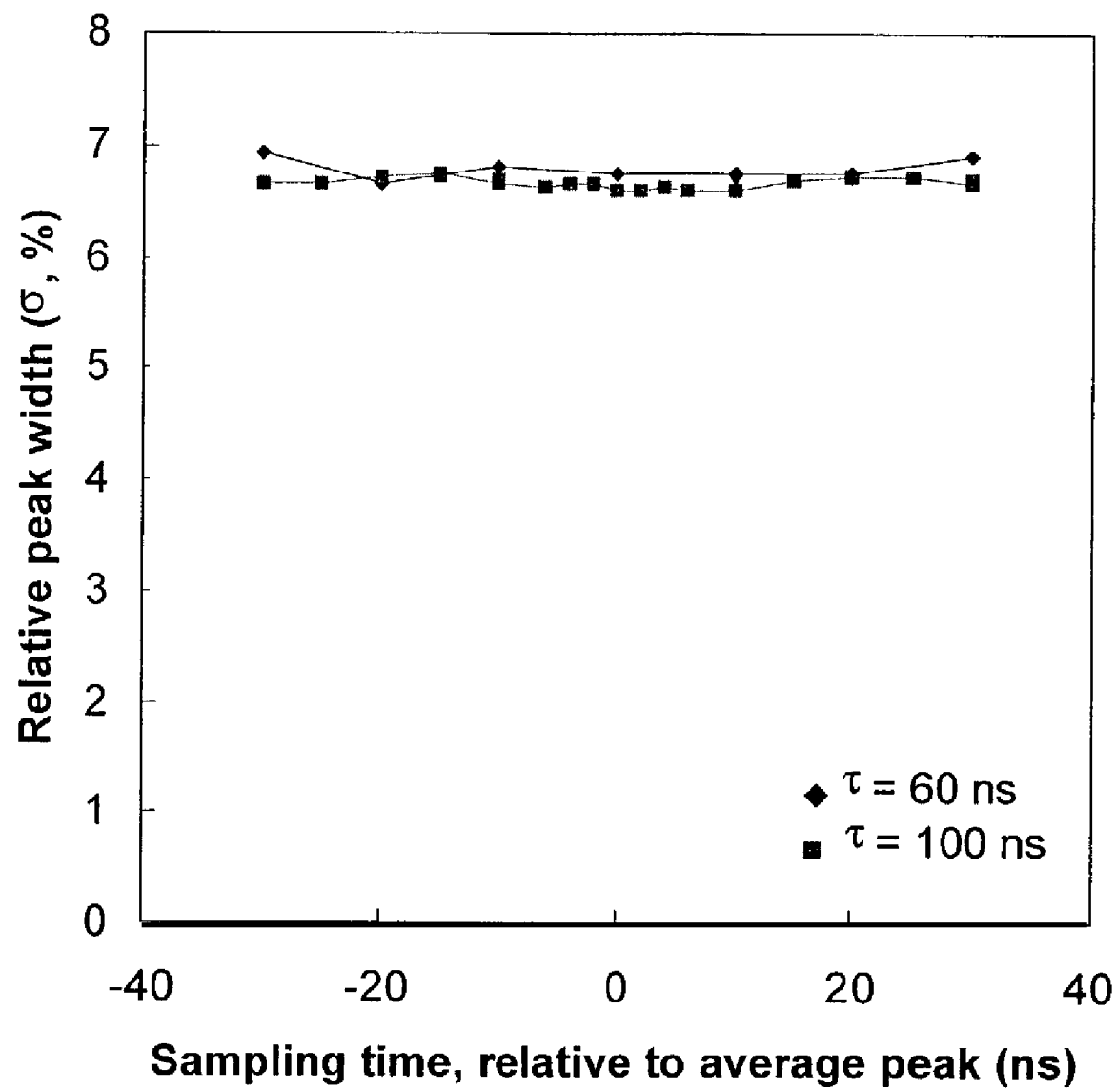
FIG. 24 is a graph of energy resolution at 662 keV as a function of sampling time.

The position of the event may be inferred from the measured front to back pulse height ratio. From our data we obtain the curve shown in FIG. 20. Over the central 16 mm of the crystal, the position resolution averages 2.86 mm FWHM if no energy cut is applied, and 2.53 mm FWHM when the energy cut is used. The position resolution degrades at the ends of the crystal, probably due to the effects of direct interactions in the APDs and to the fact that this data is taken at a constant number of events for each z position, obviously increasing the relative contribution of Compton scattered events when the main photon beam is past the end of the crystal. However, if the physical constraint that the interaction occurs inside the crystal is taken into account, then measured position FWHM around 2.5 mm can be recovered.

Figure 15:
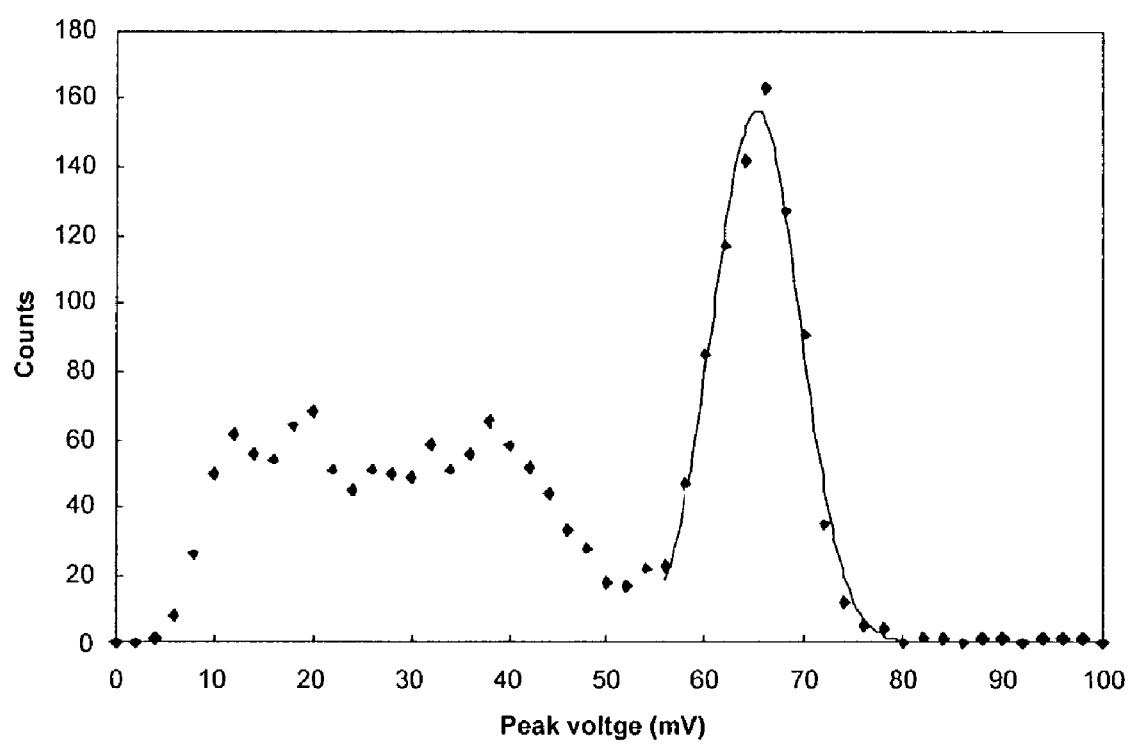
FIG. 15 is a graph of $^{22}$Na spectrum from LSO read out by a single-channel APD using prototype circuit B.

Energy resolution is also measured extensively. To discuss the energy resolution, it is useful to examine the front vs. back pulse height scatter plot. As a first approximation, the energy may be expressed as $E=\alpha F+\beta B$. The relative coefficients are determined by a line fit to the photopeak region in the scatter plot. The resulting energy spectrum is shown in FIG. 15. The energy resolution is about 14% FWHM. The observed photopeak to Compton ratio is about 0.7, which is roughly in agreement with the 0.521 expected for a small LSO scintillator. The difference probably can be attributed to the nonzero energy threshold and to multiple-interaction events.

In the front-back scatter plot two effects were clearly visible which can limit the energy resolution, at least in principle. The photopeak did not appear as a perfectly straight line, but rather is bowed in slightly in the middle region, indicating, as is to be expected, a lower light collection efficiency for events near the middle of the crystal. Also the photopeak is broadened and reduced in amplitude near the ends of the crystal, which can probably be attributed to total internal reflection from the end of the crystal. The critical angle between LSO and BC-630 grease is 53.6°, so this only begins to occur within 1.47 mm of the ends.

The depth of interaction information may be applied in an attempt to improve the energy resolution, writing the energy as $E=(\alpha F+\beta B)f(F/B)$ and determining the coefficients and the correction function $f$ from a fit to the photopeak region in the scatter plot. This technique may produce useful improvement.

Figure 11:
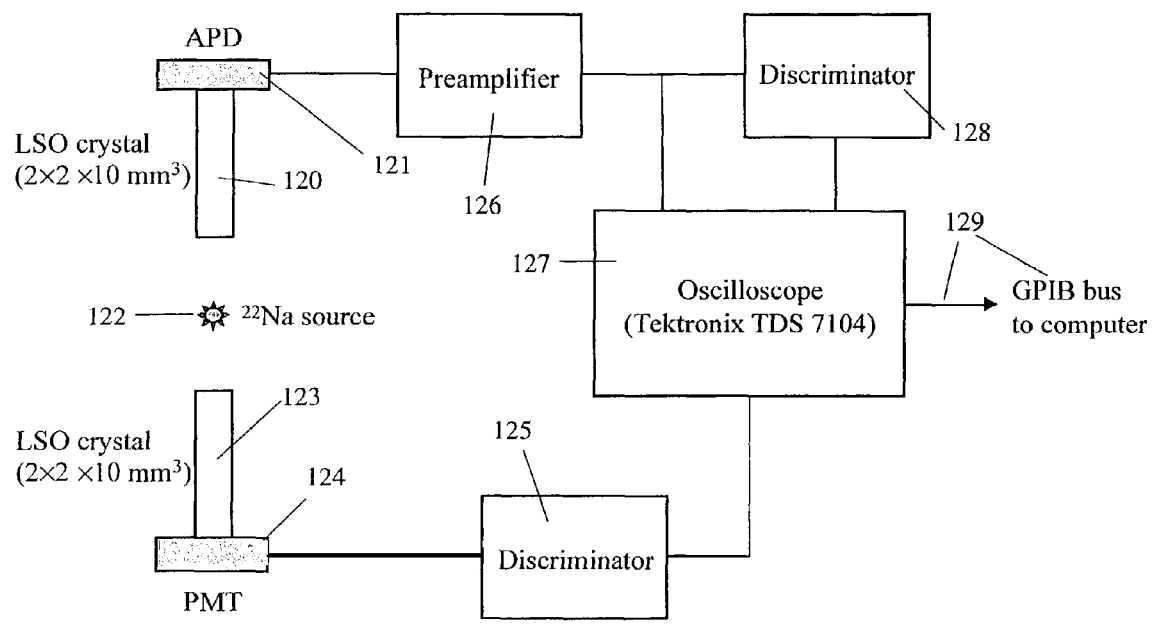
FIG. 11 is a diagram of the setup for timing and pulse height measurements.
Figure 12:
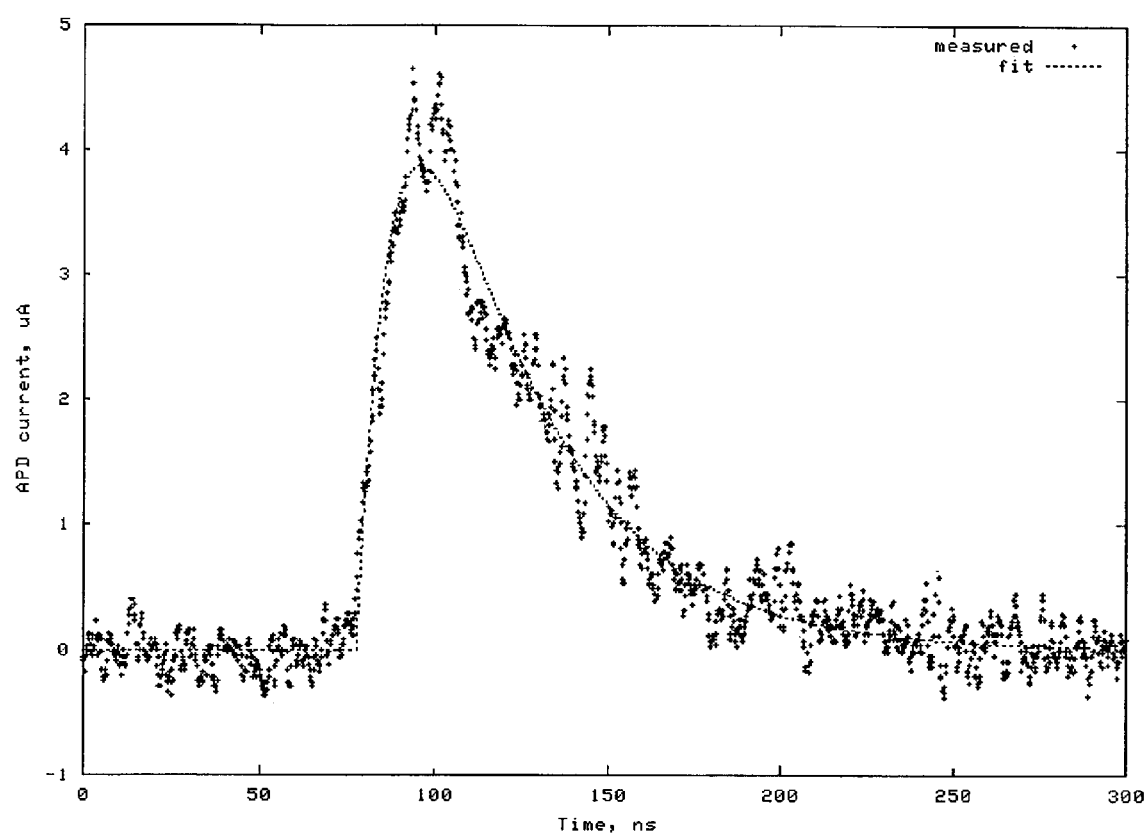
FIG. 12 is a graph of a typical APD current signal as measured by circuit A, with a $^{22}$Na source and LSO crystal. The amplitude of this pulse is typical of the photopeak.
Figure 13:
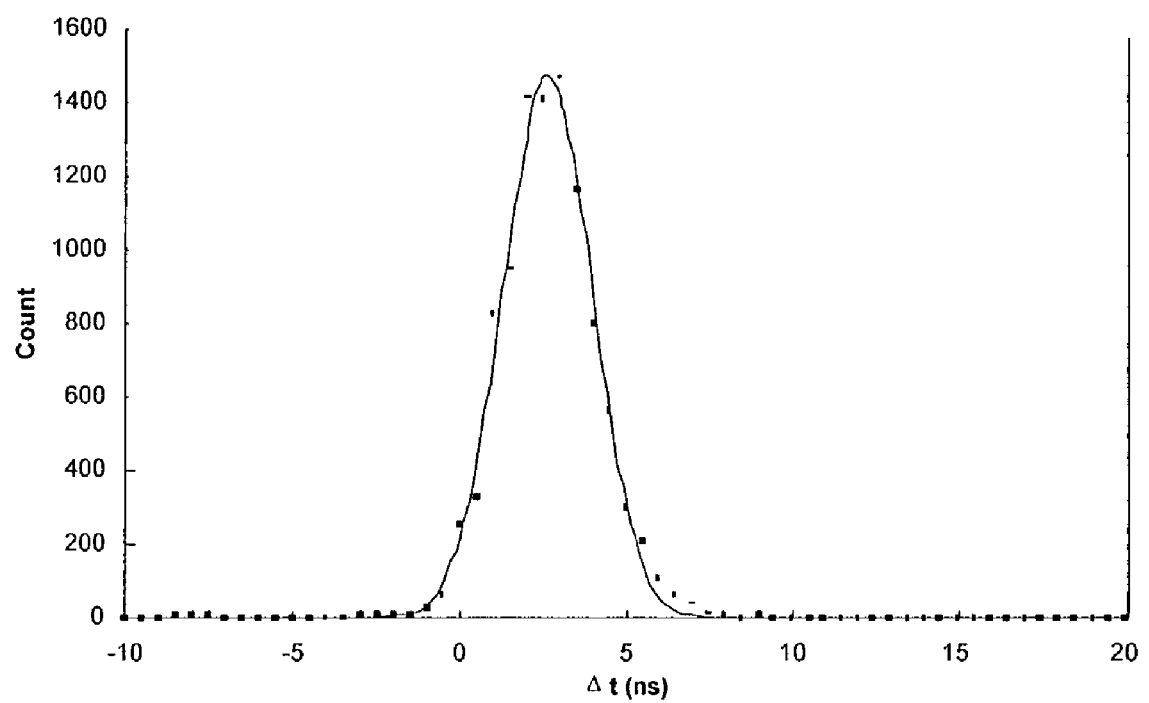
FIG. 13 is a graph of the distribution of the time difference $\Delta t = t_{APD} - t_{PMT}$ between the trigger times of the APD and PMT signals. The curve represents a Gaussian fit to the data.

We studied the coincidence time resolution (figures FIG. 13, FIG. 14, FIG. 21, FIG. 27) with the LSO/APD and LSO/ PMT detectors positioned in a line, 140 mm apart, and the source mid-way between them (FIG. 11). The time difference was measured using a TDS7104 digital oscilloscope (bandwidth 1 GHz, sample interval 200 ps) in delay measurement mode. With no explicit energy cut the coincidence time resolution is 4.6 ns FWHM. Applying a cut for greater than 250 keV, coincidence time resolution is 3.6 ns FWHM, 9.2 ns full width at one-tenth maximum (FWTM); time walk correction reduces this to 3.4 ns FWHM, 7.5 ns FWTM.

Some amount of time walk was evident at all energies, although above 250 keV the effect of time walk is minimal. If required, residual time walk correction could be applied by programmable logic resources on the detector module board or on the ASIC.

The resolution is limited by time walk in the LSO/PMT readout (left side of the peak in FIG. 21), and possibly by noise in the APD readout electronics. We addressed these issues by optimizing the amplifier bandwidth and gain, and by making direct APD/LSO-APD/LSO timing measurements.

The ASIC (application specific integrated circuit) is the crucial part of this work for producing a compact and full function PET system. FIG. 1 is an overall block diagram of the readout chip (ASIC), of which only two signal channels, 5 and 17, are shown. Additional signal channels are represented by the ellipsis 29. An input signal 1, 13 from a high-gain avalanche photodiode is sent to each signal channel. Additional inputs to each signal channel are for user-supplied timing signals $V_U$ 2, 14 and $V_V$ 3, 15, for a test signal 4, 16, and for a sample/hold control signal 22, 23 generated by the coincidence logic and sample/hold control circuit 25. In another embodiment the sample/hold circuit may be replaced by a peak/hold circuit. Each signal channel outputs signals AOUT 6, 18, UOUT 7, 19, VOUT 8, 20, and HIT 9, 21. The voltage output on AOUT 6, 18 indicates the size of the detected signal. The voltages output on UOUT 7, 19 and VOUT 8, 20 are representative of the time at which a signal was detected and may be used in the analysis of the data acquired with the readout chip to distinguish true detector signals from noise signals. These signals may also, be used for timing the arrival time of the signal or event, such as the arrival time of the x-ray or gamma ray photon. These signals are input to an analog or digital multiplexer or a shift register 10 and from there through a buffer circuit 11 to an analog-to-digital (A/D) converter 12. The HIT signal 9, 21 from signal channels 1 to n is input to the coincidence logic and sample/ hold control 25. Here 25, the HIT signals from all signal channels are combined with the signal CORR_IN 26, to decide whether the detector system has detected a valid positron emission event. CORR_IN 26 may be generated inside the chip, also called ASIC, or on the printed circuit board on which the chip is located, by forming the logical OR of the CORR_OUT signals coming from other, readout chips 28 that form part of the PET detector system. At the same time, a signal CORR_OUT 27 is distributed to the other readout chips, to be used to generate the CORR_IN signal for these chips' coincidence logic, in the same manner as described above. In another embodiment the CORR_OUT signals from different chips can be routed to a logic circuit (not shown), which makes a decision if two or more signals received by different chips are coincident or not.

Figure 4:
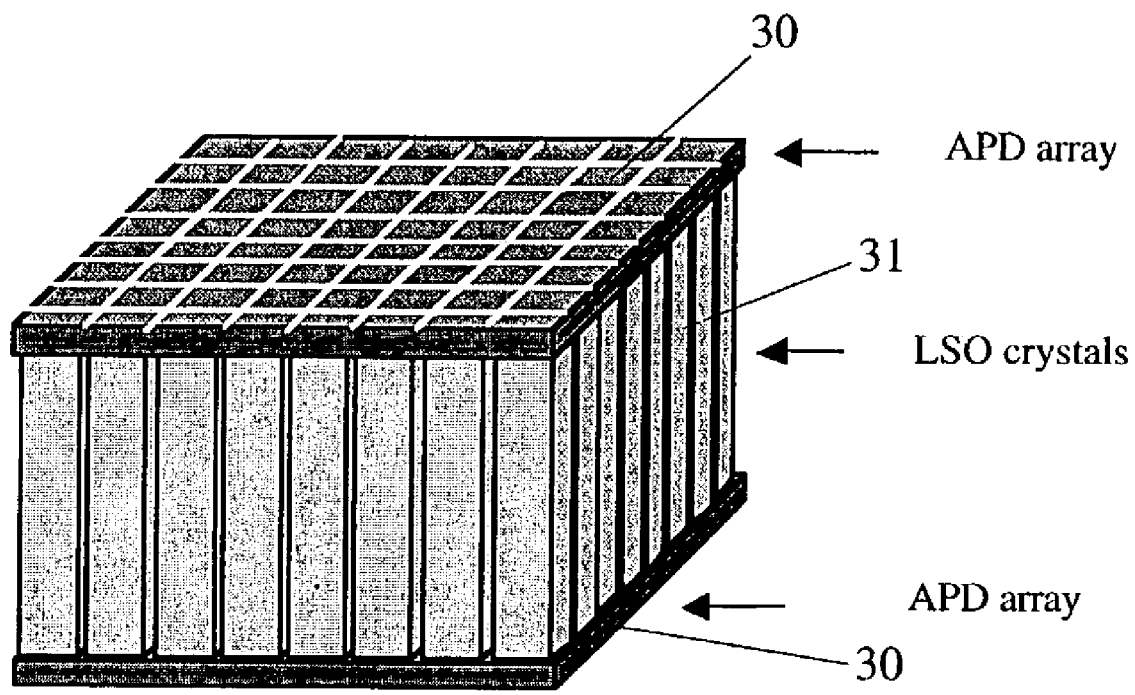
FIG. 4 is a drawing of the PET detector module concept for breast imaging using two APD arrays to read out an array of scintillator elements, providing depth of interaction information.

Coincident means that two or more gamma rays incident on two or more separate detector arrays FIG. 4 31 arrive within a short time depending on the geometry measured in nanoseconds, about 1 to 1,000 ns. Such events are well known for positron annihilation, which produces two gamma rays back-to-back. These gamma rays, therefore, travel in opposite direction at about 180° from the vertex of annihilation. Therefore, if both gamma rays are detected then the position of the positron annihilation is somewhere along the cord that connects the two detection sites or pixels. This information is used in PET to image human body especially metabolism in living tissue. There are other applications where two or more gamma rays may be generated in coincidence. The detector system developed and discussed here can be used for detection and imaging of such applications and sources. The developed system can also be used for applications where single photons are emitted by a source or an object, detected and/or imaged by the detector presented here. In such a case there is no need for coincident detection and these sections of the detector may not be used or deployed.

The ASIC has an onboard readout logic circuit (not shown) which controls all the chip's functions and also outputs the channel address(es) from which it has received a signal. This circuit can do many functions besides controlling the ASIC functions and outputting channel address(es). It can, for example, supply information and control gain; offset and threshold adjustment adjusting circuits such as digital to analog converters (DACs); assist in controlling multiplexer(s) and shift register(s); monitor chip temperature; controlling calibration and testing modes; turn on and off certain sections of the chip such as channel and test inputs; reset certain sections of the ASIC; monitor chip functionality and status; and output chip status and problems that may occur. Analog to digital (A/D) converter 12 may also be designed to reside onboard the ASIC.

Figure 10:
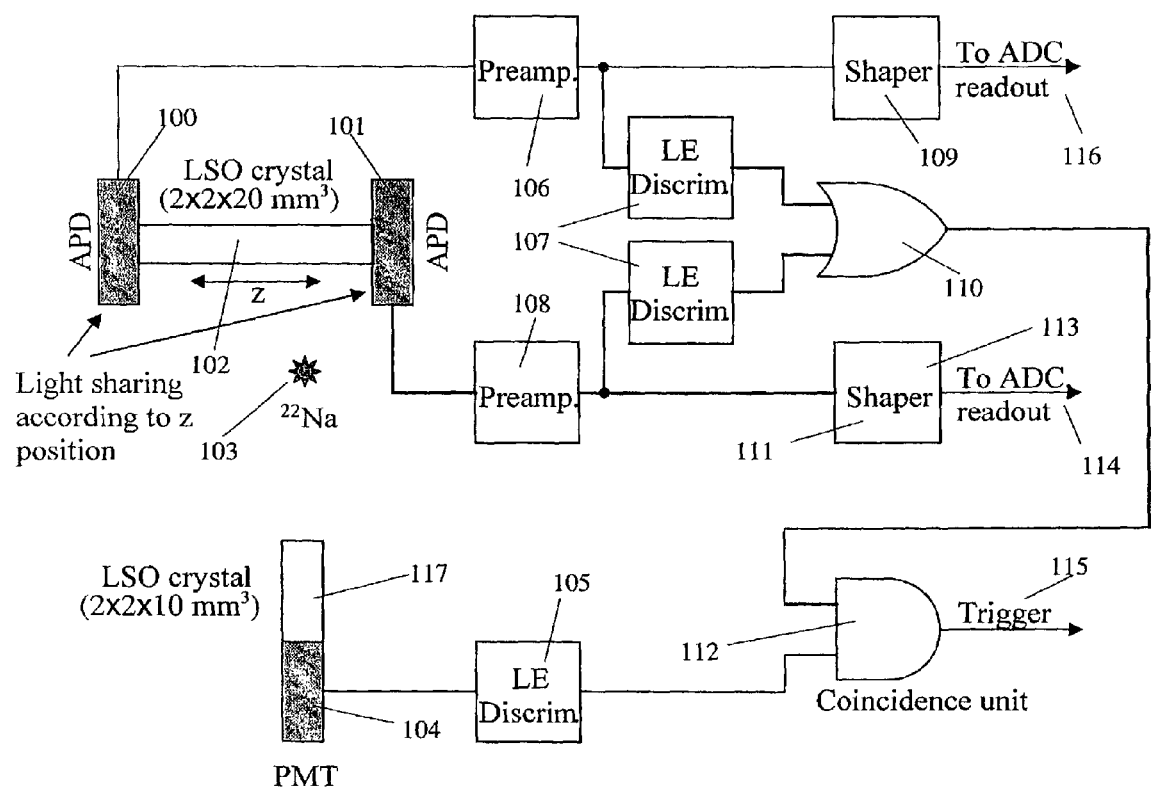
FIG. 10 is a diagram of the test setup for depth-of-interaction (DOI) measurements

The data acquisition computer will use the information from the ASICs reading out the APDs 30 on each end of the LSO detector array 31 to determine if there is a signal from the two ends of a single LSO crystal which is necessary do determine the DOI (depth of interaction) in that crystal. Figures FIG. 25 and FIG. 26 demonstrates how the array is read out and what the imaging of gamma rays looks like. FIG. 10 demonstrates the DOI principal and measurements carried out at NOVA R&D, Inc. This information limits the interaction point of the gamma ray to a small section of the crystal 102, thus eliminating radial elongation error inherent in present PET detectors which use either BGO or LSO or any other scintillator material. The post analysis of this information after the data is stored into the memory of the computer is slow and delay image processing and also requires storing extra data, which does not have signal from both sides of the LSO crystal. To solve the slowness of the data analysis, in another embodiment, the ASIC can be designed with required DOI determination circuitry on board of the chip to analyze the signals received from the APD arrays at the two ends 30 (100, 101, 102) of the LSO detector array 31. To facilitate this function the two chips from each end of the LSO array 31 can be designed to be daisy chained so that they will act as if a single ASIC. This will allow the signals from both ends of the LSO array 31 to be analyzed as if recorded inside the same ASIC. This circuit (not shown) can determine if a signal is received from the opposite ends of each LSO crystal in the array and would not produce an event trigger if they did not, thus reducing data rate, and calculating the DOI and outputting it as an analog or digital signal In another embodiment, the event trigger and/or DOI will be output only if there is a coincident event detection informed to the ASIC from other chips through the CORR_IN 26 signal.

To speed the readout time and rate the ASIC is designed to have sparse readout capability. This capability will allow the readout of the channels with signal (data) only. The other channels will not be read out. There will be a mode which will allow readout of all the channels for testing and calibration. There will be also a test mode where the analog signals will be routed to the output from the analog sections by passing the S/H circuit and other digital sections. There may be also a hit register circuit which will output the channels which have signal. This information can be used to readout channels adjacent to the channel with signal if needed.

Figure 2:
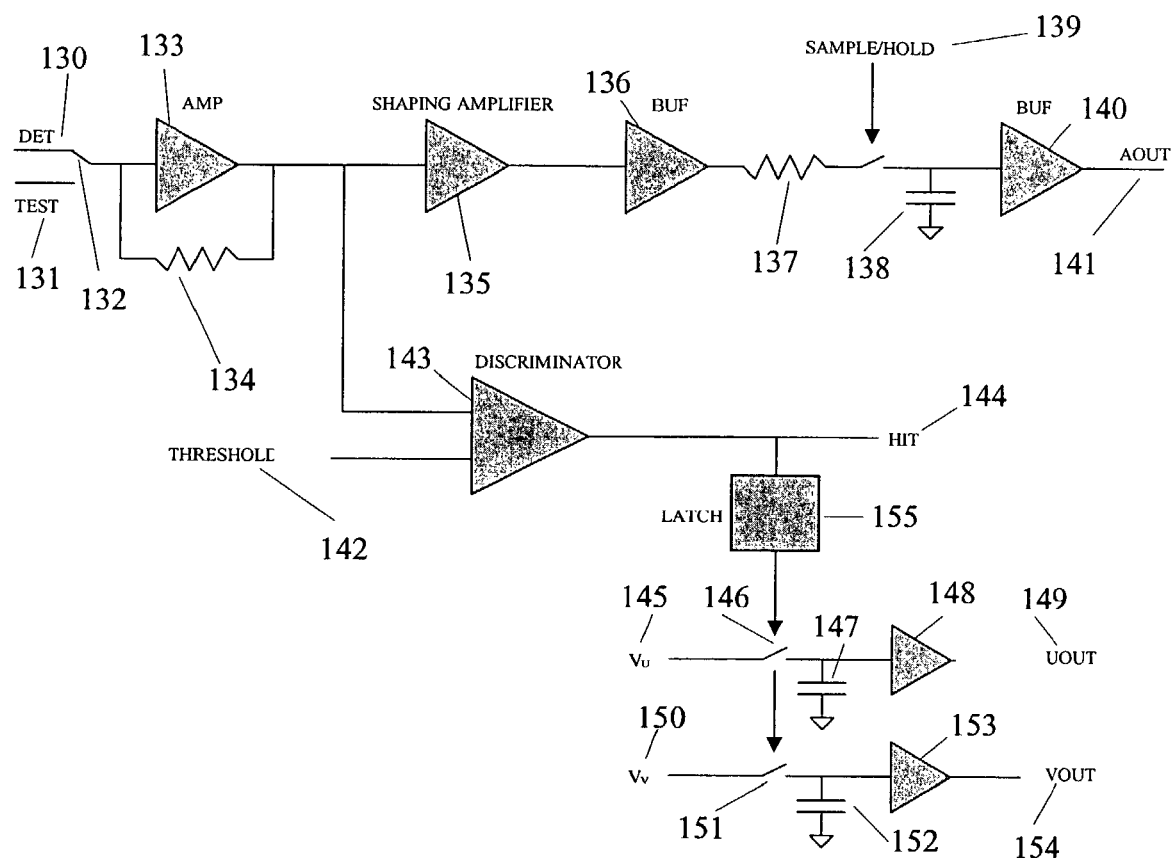
FIG. 2 is a signal channel diagram of LSO/APD PET Imaging ASIC.

The signal channel 5, 17 is shown in detail in FIG. 2. The detector signal 130 is input to a high-bandwidth transimpedance amplifier 133, with feedback resistance 134. Alternatively, a test signal 131 can be selected, via a switch 132, as input to the amplifier 133. The high bandwidth enables the amplifier 133 to faithfully reproduce the fast rise time of the detector signal 130 coming from the avalanche photodiode. Instead of APD other sensitive and fast light detectors such as a fast photodiode, a photomultiplier tube (PMT), solid state photomultiplier, or a multi anode photomultiplier tube (MAPMT) may be used. The analog output signal generated by the amplifier 133 is sent to a shaping amplifier 135 and from there to a buffer 136. The signal from the buffer 136 charges a capacitor 138 through 137 as long as the sample/hold switch 139 is closed. When the switch 139 is open, the charge is held on the capacitor 138 and is provided on the AOUT output 141 via the buffer 140. This constitutes the analog signal output. This output 141 may be digitized through an A/D converter built on the ASIC or outside the ASIC.

The output from amplifier 133 is also sent to a discriminator 143. Whenever the output voltage from amplifier 133 exceeds the voltage supplied to the threshold input 142, the HIT signal 144 will be activated. The HIT signal 144 is provided to the coincidence logic and sample/hold control 25. The HIT signal 144 is also sent to a latch 155, whose output controls switches 146 and 151, which are used to sample and hold the timing voltages $V_U$ 145 and $V_V$ 150. may be supplied to the readout chip externally or generated directly on the chip. $V_U$ 145 and $V_V$ 150 represent known time-variable (typically periodic) voltage signals. When the latch 155 is activated, it opens the switches 146 and 151, causing the momentary values of $V_U$ 145 and $V_V$ 150 to be held on capacitors 147 and 152, respectively. These values are output through buffers 148 and 153 as signals UOUT 149 and VOUT 154, which can thus be used to determine the time at which the HIT signal 144 was activated. The latch 155 is reset after readout of UOUT 149 and VOUT 154 is complete. Or latch 155 can be used to sample the $V_U$ and $V_V$ with a short gate time. This allows instantaneous sampling for some applications.

Figure 3:
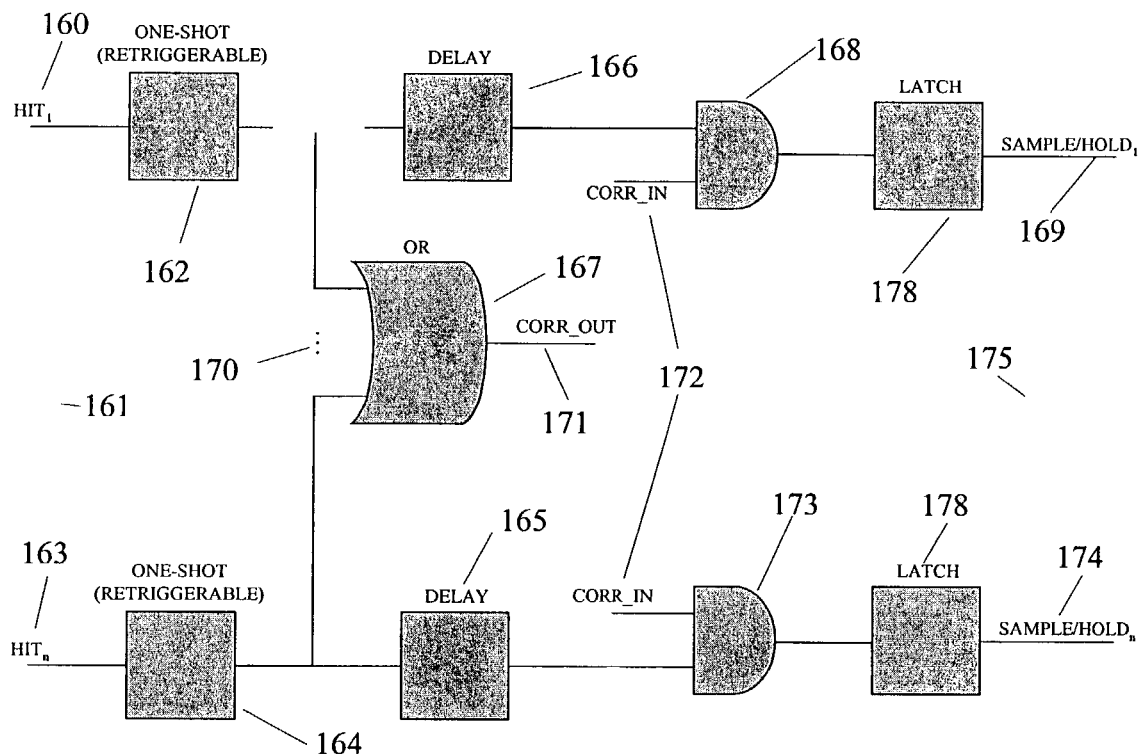
FIG. 3 is a coincidence logic diagram of LSO/APD PET Imaging ASIC.

FIG. 3 shows details of the coincidence logic and sample/hold control circuit 25. The HIT signals from all signal channels on the readout chip are input to the coincidence logic. FIG. 3 shows two HIT signals 160, 163; the signals from the other channels, as well as the signal processing paths for these signals, are represented by the ellipsis symbol 161. The coincidence logic requires signals of a well-defined duration, which are generated from the HIT signals 160, 163 by retriggerable one-shot circuits 162, 164. One-shot circuits produce a pulse whenever they are triggered, where the duration of the pulse is adjustable. From the outputs of these one-shot circuits, and those for the other channels on the readout chip, represented by the ellipsis 170, a logical OR 167 is formed. The resulting signal CORR_OUT 171 is provided to the CORR_IN signal inputs 26 of other, similar readout chips that form part of the PET detector system. CORR_IN 172 is used to form coincidences 168, 173 with the output signals from the one-shot circuits 162, 164. To compensate for the propagation delay of the CORR_IN signal 172 coming from other, identical readout chips that form part of the PET detector system, the output signals from the one-shot circuits 162, 164 have to be sent through the delay circuits 166, 165 before being input to the coincidence circuits 168, 173. Whenever a coincidence circuit 168, 173 detects a valid coincidence, a latch 177, 178 is triggered to activate the corresponding sample/hold signal 169, 174. At the same time, a readout trigger is generated and sent to the chip's readout logic (not shown). For each channel for which a valid coincidence has been detected, the readout logic then causes the multiplexer 10 to send the AOUT 6, 18, UOUT 7, 19, and VOUT 8, 20 voltages, in turn, to the output buffer 11 and from there to the A/D converter 12. The digitized voltage data, together with the channel addresses for the respective channels, are then sent to the data acquisition computer (not shown). This function can be also incorporated into an electronic circuit and implemented in real time to determine automatically the wanted events. Such hardware circuit can increase the data acquisition rate and reduce post-processing time as superfluous data will be significantly reduced.

FIG. 4 shows a diagram of a scintillator array 31 viewed from both ends by two two-dimensional APD arrays 30. The scintillator can be made of LSO, BGO, or other high Z scintillators. The APD array 30 (FIG. 5, 35) is optically connected to the array of scintillator crystals 31. The connection can be rigid using epoxies or similar compounds or can be non-rigid or flexible. The individual detector crystals 31, 102 can be left as they are or wrapped by reflecting, diffusing or nonreflecting material to reduce crosstalk aid/or improve light collection capability to improve signal to noise ratio. In another embodiment the crystals can be separated through separators placed in between crystal layers. In another embodiment, the crystal array may be a single uncut or partially cut crystal. In another embodiment the detector arrays 31 are placed on each side of an object. Or a single or multiple rings of detector arrays 31 can be placed around the object to be imaged. Septas may be placed in between or inside the detector arrays or a ring of detector arrays. Also hole or slot collimators may be placed in front or around the detector array(s) 31.

Figure 5:
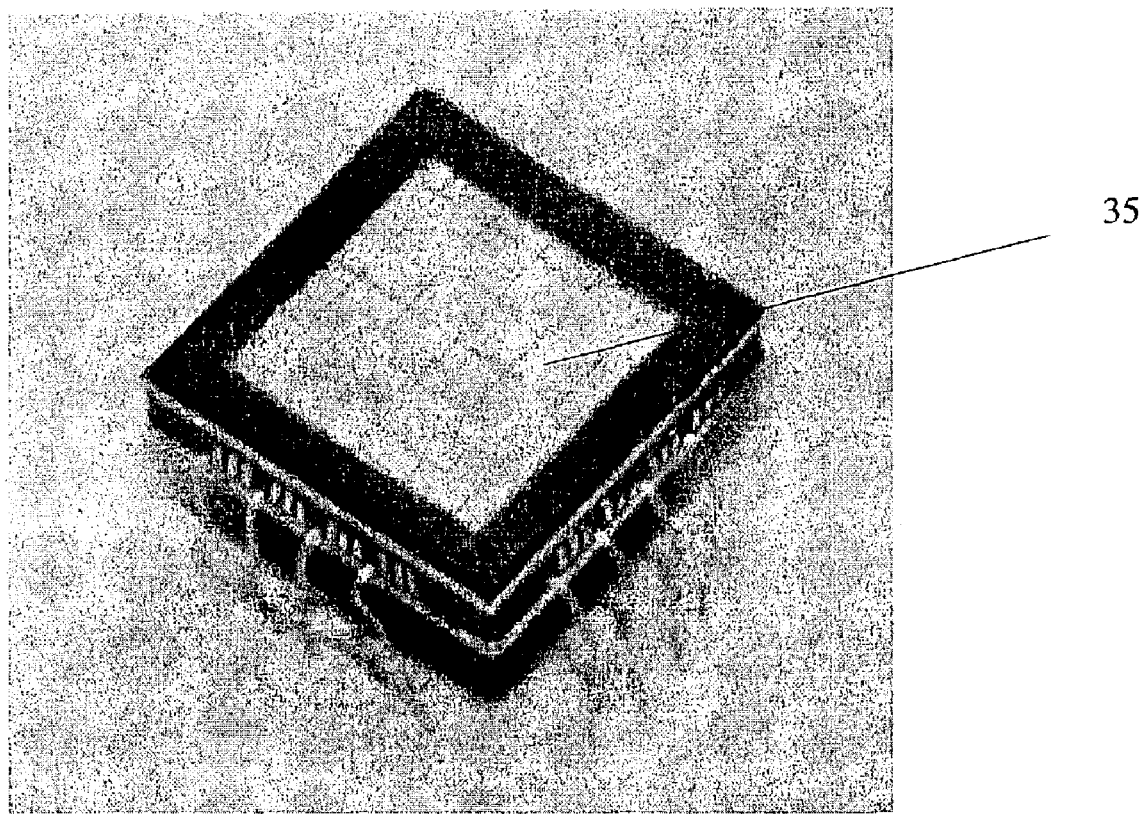
FIG. 5 is a photograph of a prototype 4×4 pixel avalanche photodiode (APD) array. Individual elements are 2×2 mm$^2$ in size. The gap between pixels is 0.4 mm.
Figure 6:
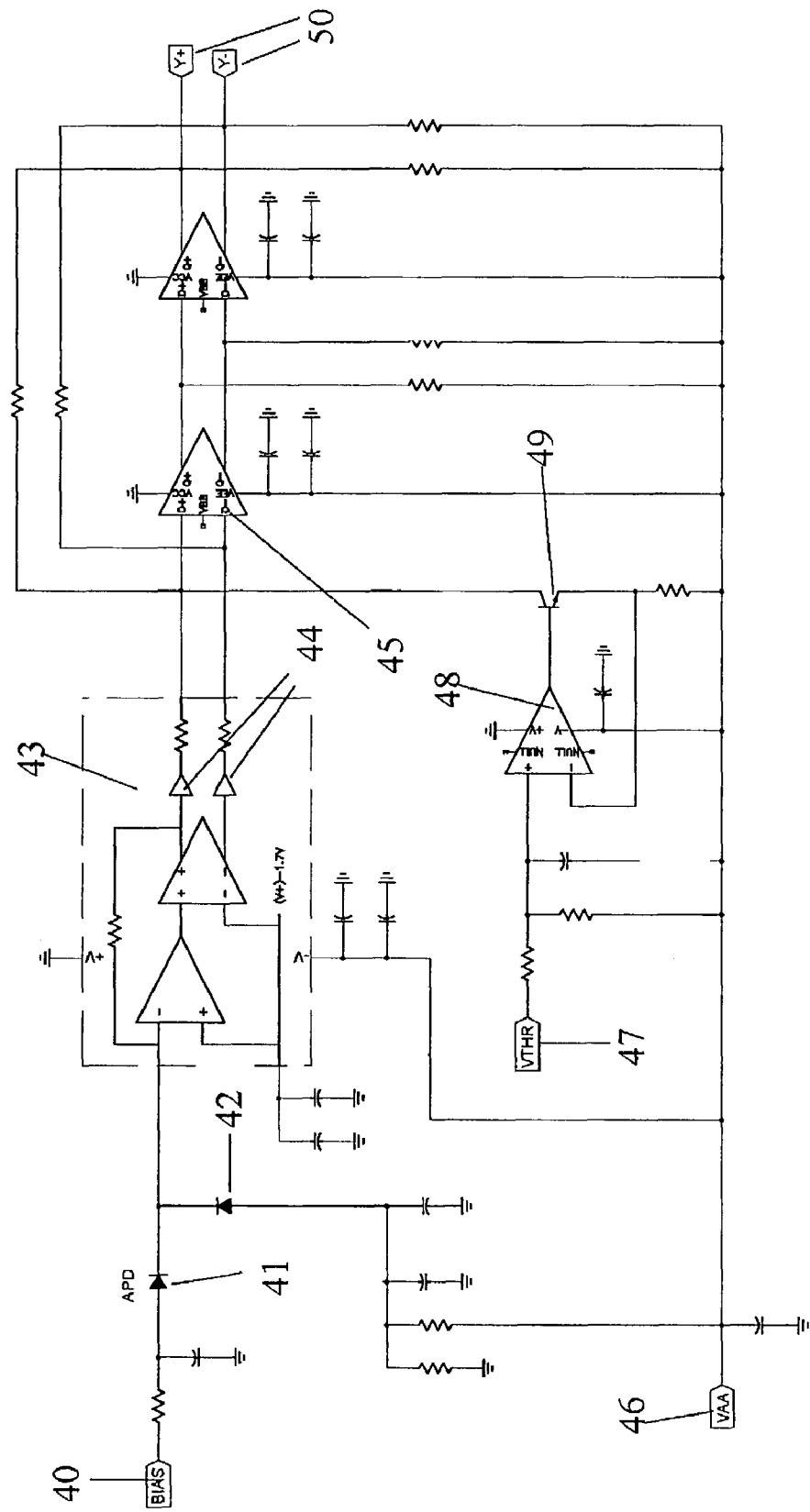
FIG. 6 is a schematic diagram of the circuit A. The APD is at the top left; the other diode is for protection against breakdown in the APD.
Figure 7:
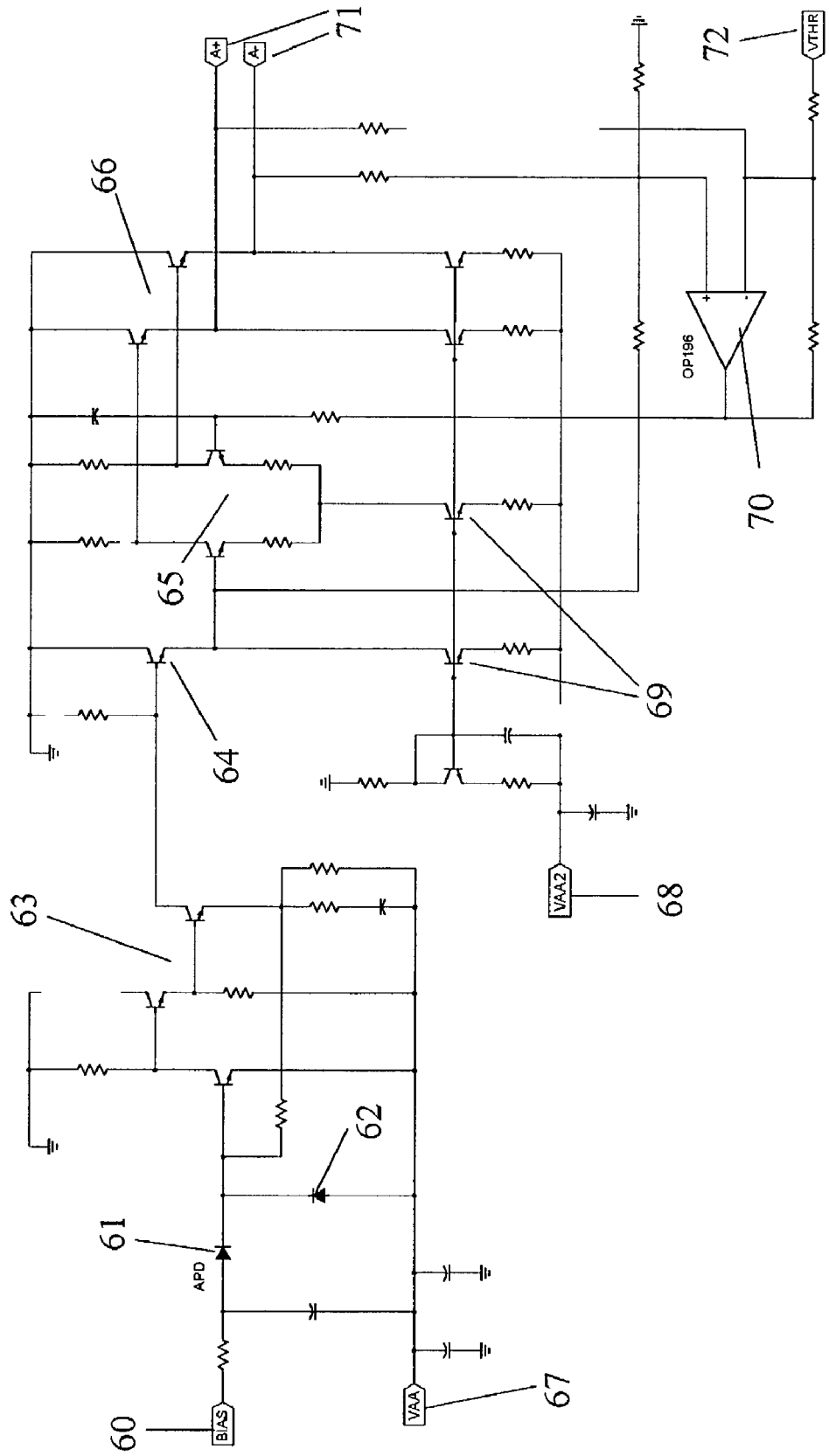
FIG. 7 is a schematic diagram of APD and connection to the 12.1 mW, 100 MHz, 56 kΩ transimpedance amplifier of prototype circuit B.

FIG. 5 is showing a photograph of an APD array 35. This is a 4×4 array of APDs built as a single monolithic block. APDs with a larger are or array can also be built. The wires coming out of the array is used to connect the APDs to the amplifier inputs 1, 13, 130. FIGS. 6 and 7 also show the APD 41, 61 connected to BIAS Voltage 40, 60 and Amplifier input 43, 63. A protection diode 42, 62 is used to protect the transimpedance amplifier 43, 63 if APD 41, 61 fails. The voltage is supplied through VAA 46, 67. A standard fast transimpedance amplifier 43 is used to make measurements using prototype circuit A (FIG. 6). A low power and low noise amplifier 63 is developed using components for prototype circuit B (FIG. 7). Differential outputs of amplifier 43 is connected to the discriminator 45 through buffers 44. Differential output 50 of discriminator is output. An amplifier 48 is used to supply an offset to the output of the amplifier 43 to form a threshold so that discriminator is not triggered if the its input does not exceed a value determined by the threshold voltage 47. The output of amplifier 48 is supplied to the discriminator input through transistor 49. This will control the threshold voltage of the discriminator. In some cases discriminator is called comparator.

FIG. 7 shows a similar circuit for FIG. 6 but it is made using individual electronic components so that it will be low power. Output of transimpedance amplifier 63 goes to a buffer 64. Buffer 64 feeds the mplified signal to an amplifier gain stage 65 which then goes into another buffer 66. The output of buffer 66 is a differential signal and it is output from the chip 71. Circuit has two power supplies VAA 67 and VAA2 68. Transistors 69 are current sources. Amplifier 70 produces the offset voltage to the analog output as discussed above using the threshold voltage VTHR 72. The outputs of the circuit shown in FIG. 7 goes into a discriminator circuit shown in FIG. 8. This circuit is also made using components so that it will be low power and fast. Low power operation is important to achieve room temperature functionality for a large multi-channel instrument. Inputs 80 to the discriminator goes into gain stages 81, 84 and 86 one after the other. In between there are buffers 83, 85 and 87. The output 91 is differential and goes to the readout electronics. Transistors 90 are current sources. Power VAA 88 supplied to the circuit. Resistors 92, 93, 94, 95 are for to produce hysteresis in the discriminator circuit.

Figure 9:
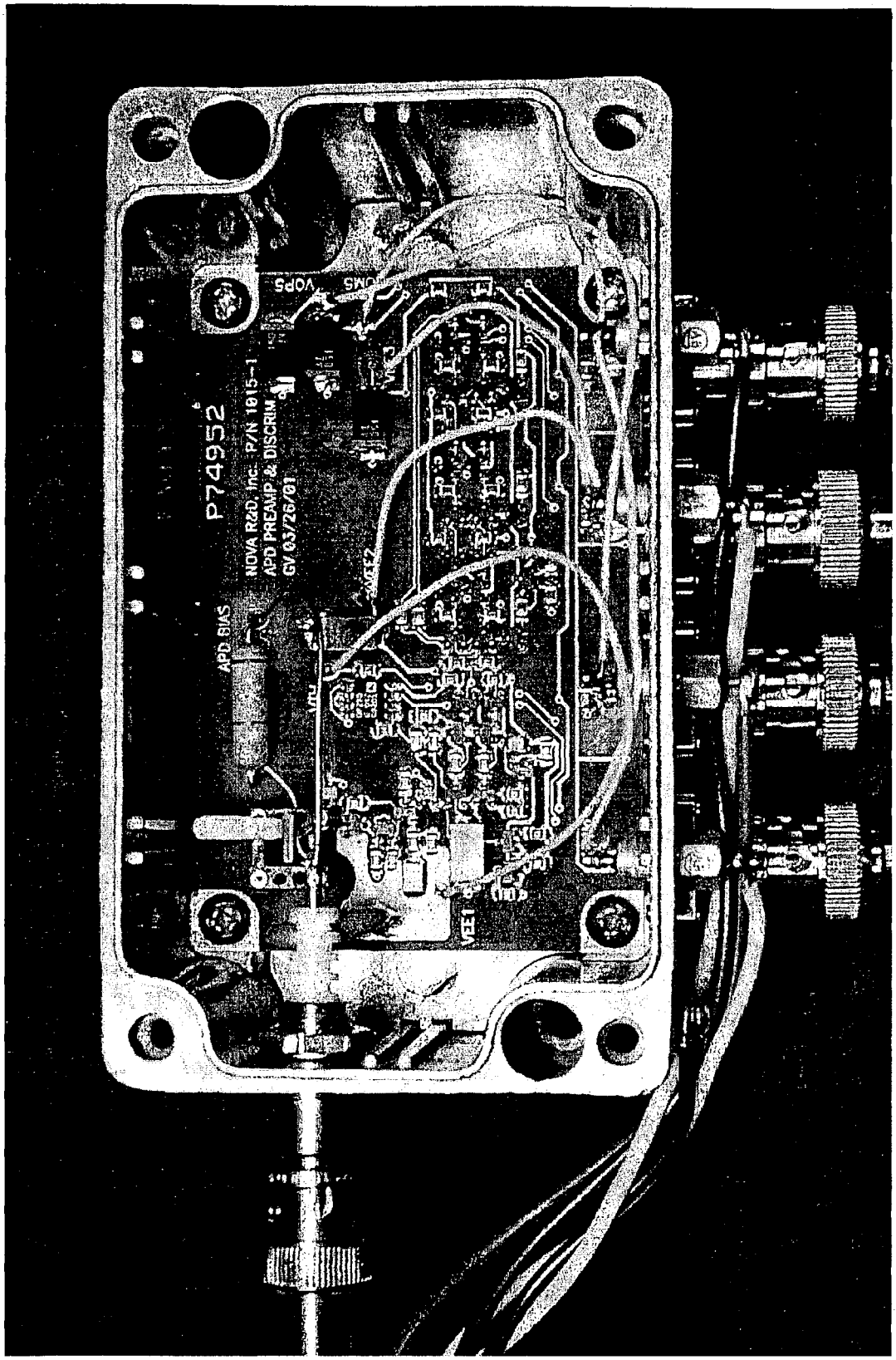
FIG. 9 is a photograph of the prototype circuit B fabricated inside a shielding box showing all the connectors and wiring.

FIG. 9 is a photograph of the prototype circuit B built for testing and demonstrating the capability of the instrument developed.

FIG. 10 shows a drawing of the test setup and circuit for the DOI measurements. The APDs 100, 101 on both ends of the detector crystal 102 detect the light produced in the crystal 102 by gamma ray coming from $^{22}$Na source 103. $^{22}$Na source 103 is a positron emitter which annihilates in the material when comes into contact with an electron and emits two gamma rays with energy of 511 keV. The second gamma ray is detected by the second LSO crystal 117 mounted on a PMT 104. The second crystal 117 defines a direction for the gamma rays emitted back-to-back and therefore the first gamma ray detected inside a small section of detector crystal 102 at a set depth. This depth is measured and first gamma ray generated light is detected by both APDs 100, 101 simultaneously. APD converts the light signal into electrons. The electron pulses are amplified by preamps 106, 108 and turned into signals. The two signals go to shapers 109, 111. Shaper circuits shape the signal into inverted or non-inverted bell shape and output. Output of the shaper circuits 109, 111 go to separate analog-to-digital converters ADC 114, 116. the pulse height of these signals are measured by the ADCs 114, 116. The output of the preamplifiers 106, 108 also go to two leading edge (LE) discriminators 107. The output of the leading edge (LE) discriminator 107 goes to coincidence unit 112. The output of the PMT 104 also goes to a third LE discriminator unit 105. Output of LE discriminator also goes to the coincidence unit 112. Coincidence unit produces a trigger signal 115 which means that two gamma rays have been detected simultaneously coming from $^{22}$Na source 103 at the detector crystals 102, 117. The ADC 114, 116 outputs from coincident events as determined by the trigger signal 115 are used to calculate the depth-of-interaction (DOI) for the gamma ray detected inside detector crystal 102. The DOI results obtained from these measurements are shown in figures FIG. 18, FIG. 19 and FIG. 20.

FIG. 11 shows a diagram of the setup used to carry out timing and pulse height measurements. Two detector crystals 120, 123 are used. The detector 120 is mounted on an APD 121 and detector 123 is mounted on a PMT 124. The output of APD 121 goes to a preamplifier 126. Output of the preamplifier 126 goes both to a discriminator 128 and an oscilloscope 127. Output of discriminator 128 goes to oscilloscope 127. The output of detector 124 goes to a second discriminator 125. Output of the second discriminator goes to the oscilloscope 127. The output of oscilloscope 127 goes to a computer through a GPIB bus 129. This circuit is used to carry out timing and pulse height measurements. The results of such measurements are shown in figures FIG. 12, FIG. 13, FIG. 14 FIG. 15, FIG. 16, FIG. 17, FIG. 21, FIG. 22, FIG. 23, FIG. 24 and FIG. 27.

An ASIC design is developed which is optimized to read out high-gain, fast APD arrays for use with LSO scintillator in PET imaging, and to build a prototype PET module based on this ASIC. Presently, no multichannel fast readout chips for APD arrays are commercially available, and even those that were developed non-commercially typically do not match the characteristics of the high gain low noise RMD APDs. Chips that were not specifically developed for APD readout lack one or more of the required features, such as a fast, low jitter trigger output or the input capacitance or dynamic range to match the APD characteristics. The developed chip will also have other applications for readout of APD arrays and multi-anode PMTs wherever fast, accurate timing is required.

In designing the readout electronics for an LSO/APD based PET system, the main consideration was to obtain high-resolution coincidence timing. This is required to achieve the combination of high singles count rates and low accidental coincidence rates that is needed for high-contrast PET imaging. Spurious coincidences create an image background by yielding reconstructed photon directions that have no correlation with the actual source distribution. By a rough estimate, we expect a singles rate of about 1.5 million counts/s in a PET system consisting of an 18 cm diameter, 2 cm axial length detector ring (2,000 pixels) for a 10 mCi injection. Assuming that these counts are evenly distributed over all pixels and that coincidences are formed between each module and a 120° ring section across from it (for a field of view of half the ring diameter), this leads to an accidental coincidence rate of 750 counts/s, per nanosecond timing resolution. This has to be compared to an estimated true coincidence rate of 10-15 kcounts/s. Our measurements demonstrated that a coincidence timing resolution of better than 2 ns FWHM is achievable for coincidences between an APD and a (significantly faster) PMT. By taking coincidences between two APDs instead, we expect the width to increase by no more than 50%. Based on that, and the system requirements outlined above require a coincidence timing resolution<3 ns FWHM measured between two APD channels with a positron annihilation source and 2×2×20 mm$^3$ LSO crystals.

Figure 8:
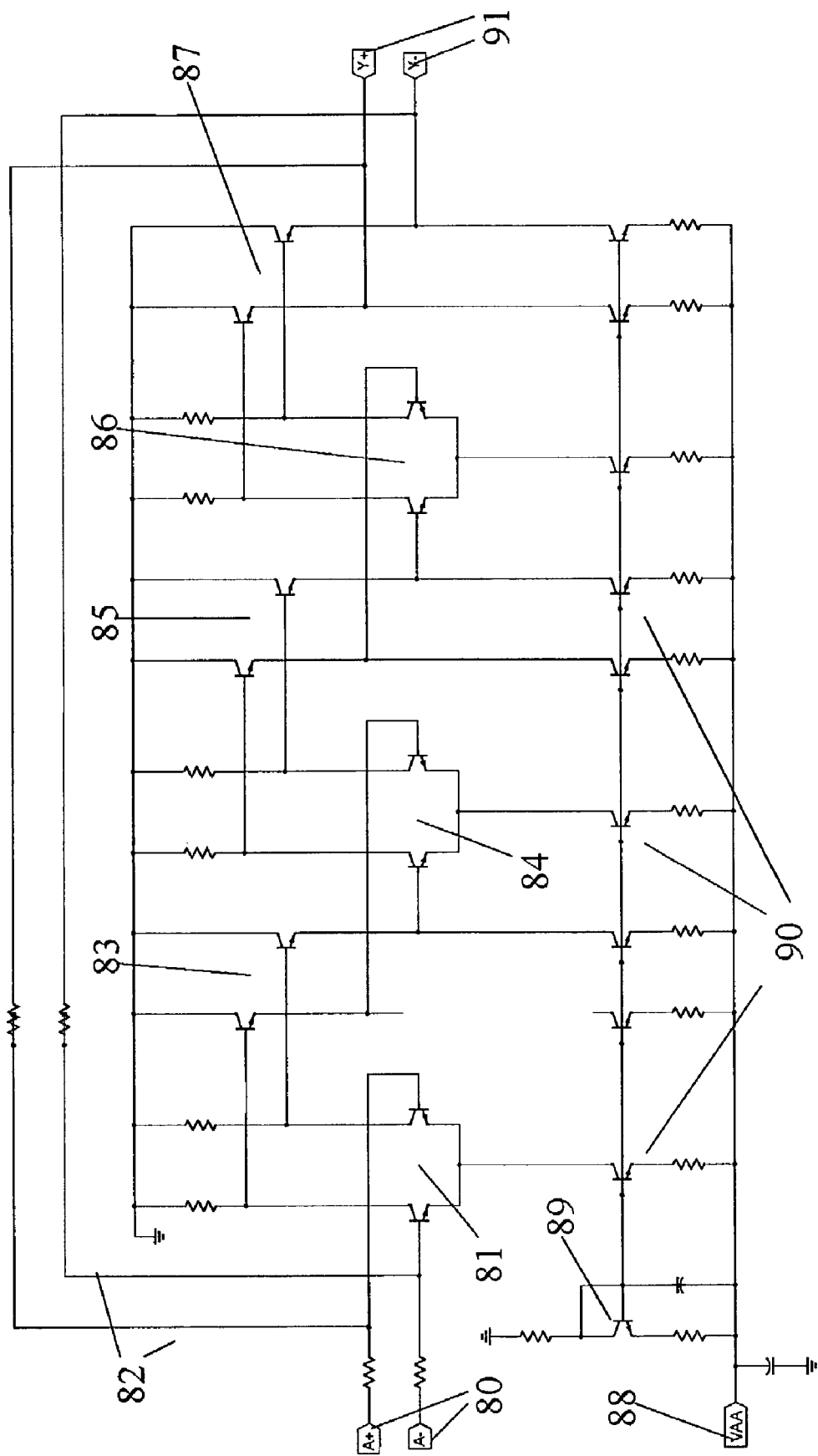
FIG. 8 is a schematic diagram of the discriminator (10.1 mW) of prototype circuit B.

To achieve the goal of high-resolution timing, we have improved the preamplifier and the timing discriminator, FIG. 7 and FIG. 8, respectively. As discussed above, a low-noise, fast preamplifier will help improve timing resolution in two ways, by reducing the (noise-induced) amplitude variations that invariably translate into timing fluctuations, and by minimizing (by virtue of a fast signal rise time) the direct slope-induced time walk, for instance in a leading edge level crossing discriminator. Based on our results, a leading edge discriminator design will be sufficient for obtaining good timing resolution; this will keep chip's power dissipation low. However, other discriminator or comparator designs may be used such as constant fraction discriminator, which has better timing accuracy and low timing jitter than the leading edge discriminator for fast pulses. A constant fraction discriminator or another discriminator, which takes into account the pulse height difference between different pulses, may be used in this application either integrated onto the ASIC our built outside.

In order to make a practical large-scale high-resolution coincidence system, it is also necessary to address the issue of controlling signal-independent systematic variations from channel to channel in propagation delay (and therefore also in signal baseline and discriminator threshold, at least with leading edge discrimination). To do so, we minimized the variations and more importantly their temperature coefficients, and also implemented delay tuning circuitry on a channel-by-channel basis to line up the discriminator outputs in the coincidence logic.

Energy measurement of each pulse is also important, in order to reject the background from scatter within the imaged object or other material. However, only a modest energy resolution is already sufficient for this purpose. As discussed above, our work with this APD has yielded an energy resolution of approximately 15% FWHM at 511 keV, and we expect at most minor changes to this value in the ASIC, due, for example, to further optimization of the shaper parameters or unexpected noise pickup.

For maximum sensitivity, and hence minimum total dose to the patient, at high event rates it is very important that the front end electronics and readout system impose the minimum practical dead time due to event processing. We took this into account in the design of the readout circuitry, and expect to meet a deadtime specification of no more than 200 to 300 ns per hit, and furthermore that this deadtime will only apply to the channels which are hit, not to an entire APD module or readout group.

Figure 14:
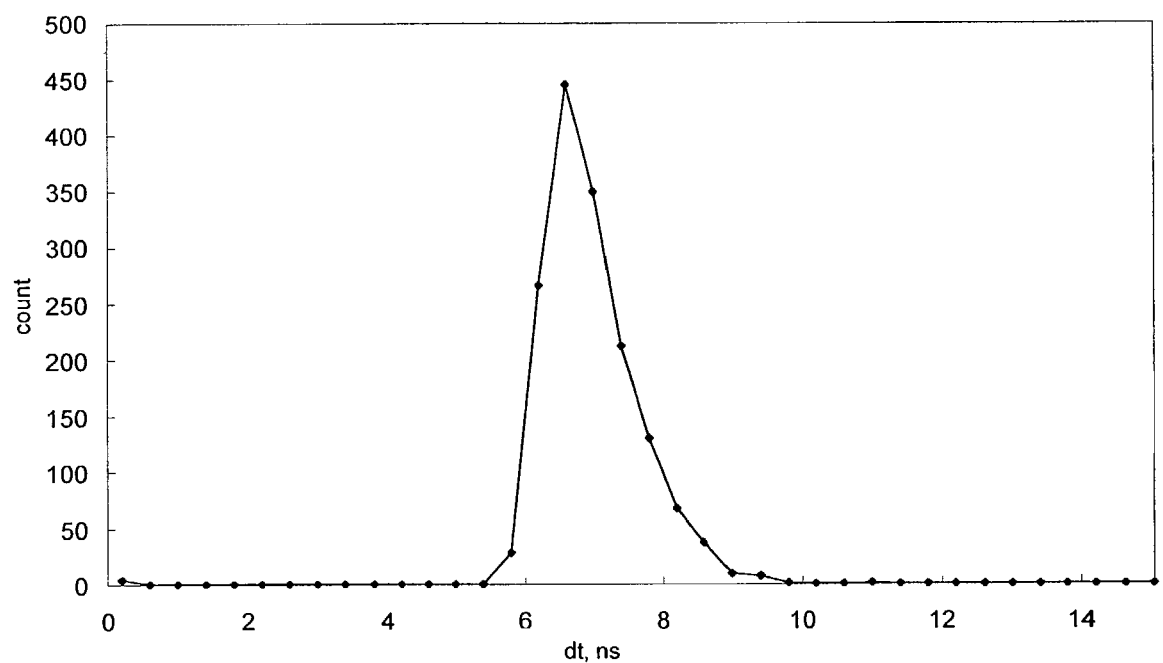
FIG. 14 is a graph of the distribution of the time difference $\Delta t = t_{APD} - t_{PMT}$ between the trigger times of the APD and PMT signals after a pulse height cut corresponding to an energy deposit of at least 300 keV detected by the APD.
Figure 27:
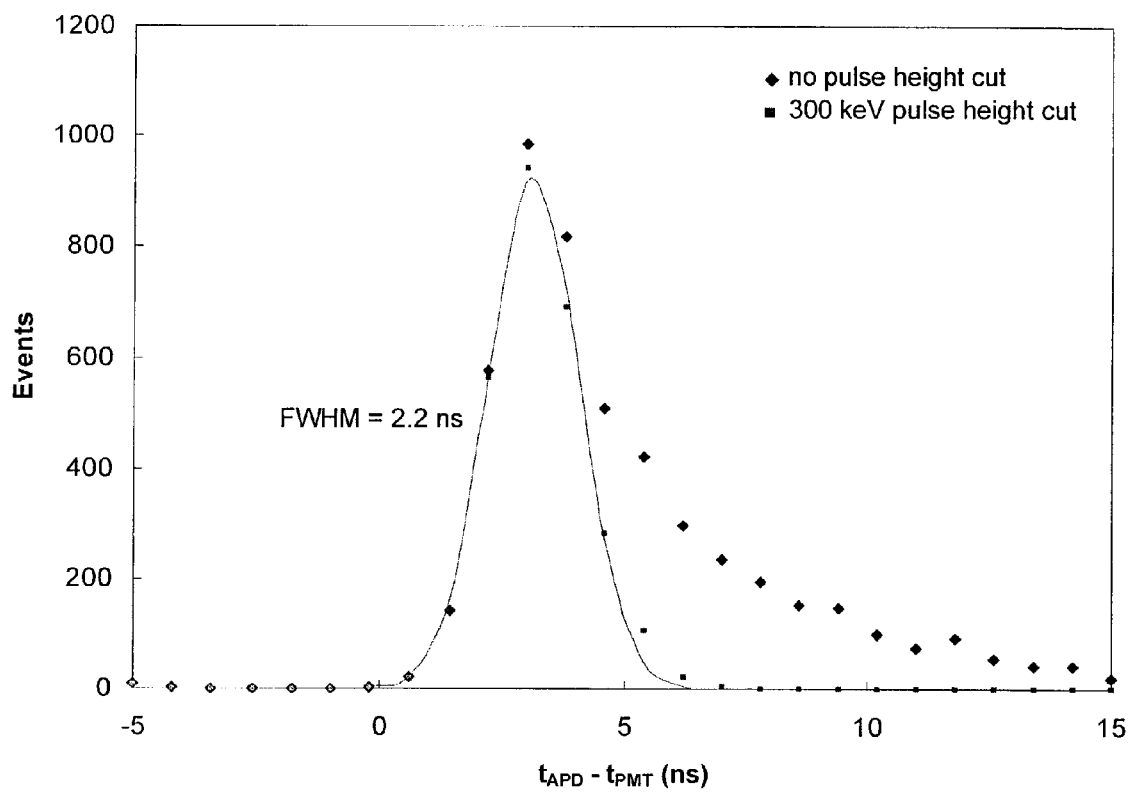
FIG. 27 is a graph of timing resolution, APD vs. PMT showing the excellent timing that was obtained using APDs.

Timing, measured relative to a second LSO crystal and a Hamamatsu R1635 PMT, is shown in FIG. 14 and FIG. 27. An energy cut at 300 keV is used. The resolution is 1.5 ns FWHM and 2.7 ns FW at one tenth maximum. The energy spectrum is shown in FIG. 15, with a resolution of 13.6% FWHM at the 511 keV.

Tables 1 to 4 summarize the achievements, energy measurements, readout electronics specifications and ASIC specifications.

Table 1

Achievements

1. Timing, energy, and depth-of-interaction resolutions for readout of 2×2 mm$^2$ cross section LSO crystals using avalanche photodiodes achieved.

2. A discrete electronics prototype DOI LSO PET detector element implementing the required readout functions efficiently, from the point of view both of circuit complexity and power dissipation is constructed. This prototype uses a single 2×2×20 mm$^3$ LSO crystal and an APD on the front and back ends.

3. Energy, depth-of-interaction, and timing resolution of the prototype system is measured.

4. A readout ASIC to implement the functions tested in the prototype system is designed.

Table 2

Energy Measurement and Shaper Design

1. Because a transimpedance preamplifier is used, and the dominant noise source is the APD, the preamplifier output noise is essentially white, and optimal response may be expected with any shaper with a peaking time greater than about 40 ns, the decay time of LSO scintillation. This has been verified by studying a fixed data set with varying shapers, as follows:

2. Feed APD preamplifier and discriminator signals and PMT discriminator signal into oscilloscope.

3. Trigger on coincidence between discriminator signals.

4. For each trigger, acquire digitized waveform data into computer.

5. For pulse-height analysis, apply an R-C filter to the preamplifier data (in software); peak-detect the result or sample at a fixed time after the trigger.

6. Determine energy resolution as a function of shaping time and, for fixed τ, as a function of sampling time.

Table 3

Readout Electronics Specifications (for ASIC and for Prototype)

1. Transimpedance preamplifier: bandwidth 60 to 80 MHz, noise<30 nA rms @ 5 pF input loading, transimpedance 40 kΩ.
2. Leading edge discriminator: threshold≈40 keV (adjustable), time walk<2.5 ns for pulses>250 keV.
3. Time pick-off: from discriminator on front or back APDs (whichever fires first); double-pulse resolution<100 ns.
4. Pulse height measurement: 2-pole shaper amplifier (150-200 ns peaking time) and sample/hold circuit.
5. Sparse readout system, using external analog-to-digital converter; deadtime can be less than 300 ns (depending on ADC speed)
6. Power dissipation: <20 mW/channel for preamplifier and discriminator.
7. Also on the detector board, external to ASIC: coincidence logic, delay tuning, list-mode data buffering FIFO, LVDS data interface, count rate monitoring scalers, local HV regulator (1,900 V input, 1,600-1,800 V output, 50 mV stability), APD gain monitoring, temperature monitoring.

BiCMOS processes to achieve such high speed and large bandwidth necessary for this application.

Figure 25:
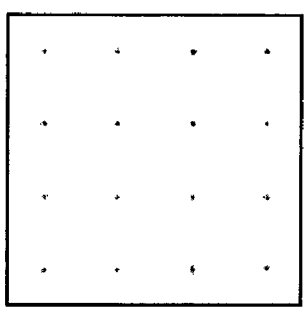
FIG. 25 is a graph of crystal identification measured with an array of 2×2×10 mm$^3$ LSO crystals coupled to the APD array and read out by the RENA™ (Readout Electronics for Nuclear Application) signal processor. The image on the left is a flood source histogram of the array, and the plot on the right is a profile across one row of the crystal array.
Figure 25:
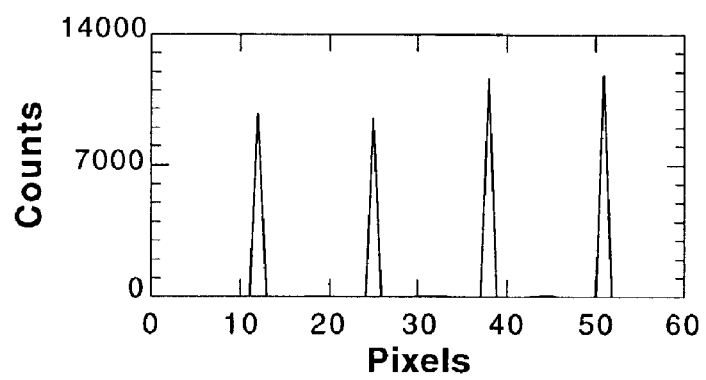

The crystal identification was studied with the same setup, and is shown in FIG. 25, which is showing a graph of crystal identification measured with an array of 2×2×10 mm$^3$ LSO crystals coupled to the APD array and read out by the RENA (Readout Electronics for Nuclear Application) signal processor developed at NOVA R&D, Inc. The image on the left is a flood source histogram of the array, and the plot on the right is a profile across one row of the crystal array. All 16 crystals are very well separated, the average peak-to-valley ratio is over 100:1 as measured from a profile across one crystal row in the image. Although events were collected with a relatively high hardware threshold, the results still demonstrate the minimal inter-channel crosstalk and excellent crystal identification.

Figure 26:
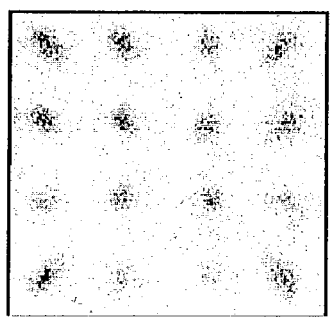
FIG. 26 is a graph of crystal identification measured with an array of 2×2×10 mm$^3$ LSO crystals coupled to the APD array and read out by two HQV802-M hybrids with multiplexed readout. The image on the left is a flood source histogram of the array, and the plot on the right is a profile across one row of the crystal array.
Figure 26:
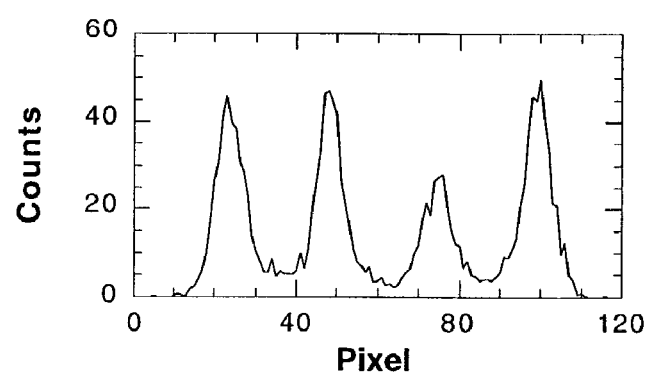

The flood source image acquired from the signal multiplexing board based on the HQV802-M preamplifiers with the same crystal array is shown in FIG. 26, which is showing a graph of crystal identification measured with an array of 2×2×10 mm$^3$ LSO crystals coupled to the APD array and read out by two HQV802-M hybrids with multiplexed readout. The image on the left is a flood source histogram of the array, and the plot on the right is a profile across one row of the

TABLE 4

| LSO/APD PET Imaging ASIC Preliminary Specifications | | |
|---|---|---|
| Input Stage | Transimpedance | 40 kΩ |
| | −3 dB bandwidth | 80 MHz |
| | Linear input signal range | 0 to −20 µA |
| | Overload recovery time (from −600 µA, 10 ns pulse) | <500 ns |
| | Total wideband output noise, input-referred (with 5 pF loading on input, no APD) | <25 nA rms |
| | Slew rate, input-referred | >4 kA/s |
| | Linearity (overall for amplitude measurement, LSO pulse shape only; direct pulses may violate this) | 2% |
| Discriminator | Sensitivity (includes hysteresis) | <15 mV |
| | Propagation delay dispersion (10 mV to 500 mV overdrive) | <1.5 ns |
| | Propagation delay | <8 ns |
| Shaper | Shaper filter time constant | 100 ns |
| General | Power dissipation | <20 mW/channel |
| | Channel count | 16-128 |

A prototype of the transimpedance preamplifier and the discriminator has been constructed and used for measurements with an LSO crystal and a single channel APD FIG. 11. The prototype is implemented in bipolar technology, which has the advantage of high speed/power efficiency; the much lower current noise capability of CMOS is not important here, relative to the APD current noise level. Furthermore, bipolar technology allows for easy prototyping with discrete components. The input stage is a current amplifier with a gain of 45. This is followed by a further gain stage and then the leading edge level crossing discriminator 126, implemented as a fully differential ECL-type circuit. The input referred wideband noise is 25 nA rms (a signal to noise ratio of 160 for the 511 keV photopeak). The bandwidth is 67 MHz. The amplifier reported here is similar to other designs for photodiode readout for fiberoptic data communications and for wire chamber readout. Transimpedance amplifiers used before specifically optimized for APD PET applications, although with a 38 mW power dissipation, and a bandwidth of 22 MHz, which would compromise the ability to get sufficient timing resolution with a simple leading edge level crossing discriminator. Therefore, the ASIC can be also designed using small width CMOS or crystal array. This image is much poorer than the previous one in FIG. 25. This is mainly due to the fact that noise from all APD channels was added together in the board to determine which crystal was hit. The lower energy threshold (~150 keV) used in this experiment might contribute to signal spreading and background in the flood histogram as well. Nevertheless, all crystals are clearly identified with an average peak-to-valley ratio about 12:1. FIG. 25 shows the superior images obtained by the RENA chip based readout system. Therefore, this measurement clearly shows that in order to take full advantage of the APD array, integrated electronics with independent signal processing must be used as seen here for the RENA results. In systems with large numbers of channels, this will require particular attention to cost considerations and issues related to power dissipation.

Input amplifier is the most important part of the ASIC. Input stage of the ASIC must be carefully designed to match the characteristics of the APD in order to achieve minimum noise. Since the primary objective is to maximize timing performance versus power dissipation, the input stage will be based on an n-channel MOSFET, which has higher transconductance and therefore lower voltage noise due to channel thermal fluctuations. The greater 1/f noise of an n-channel versus p-channel MOSFET will not be detrimental to timing because it will be dominated by the APD leakage current shot noise within the passband of the fast shaper used in the timing signal path. The size of the input transistor is carefully chosen, based on the expected APD (4 pF) and stray capacitances, to optimize the voltage noise contribution to the overall noise—too large a transistor will increase the equivalent noise charge of the amplifier because of excessive capacitance, whereas too small a transistor will have insufficient transconductance and so a large voltage noise and therefore the amplifier will have a large equivalent noise charge. Consideration will also be given to the possibility of operating the input transistor at the edge of weak inversion, where the transconductance versus bias current is maximized. To achieve the required timing spec, the input amplifier must also have a fast risetime and good linearity, and the fast shaper amplifier must also have good linearity. The preamplifier requirements for this APD array are similar to (although not identical with) those which have been reported. These authors have reported excellent timing performance (although their chips do not yet integrate a timing discriminator), and therefore it is certainly feasible to design the required preamp in CMOS technology. Important to that will be laboratory measurements, with a very wideband amplifier, of the APD signal shape in combination with LSO, a positron source, and a fast scintillator and photomultiplier tube. The optimum shaping time depends on the variations in the APD charge collection, which this measurement will determine, and also on the relative magnitude of the APD leakage current shot noise and the input amplifier voltage noise. The optimum shaping time (for timing measurement) is on the order of 5 to 10 ns.

A selectable gain circuit will be included in the signal path, so that different APD gains can be accommodated and so that we can study the optimal operating point of this APD for LSO based PET imaging.

Discriminator is also an important part of the ASIC. It is well known that the use of a simple leading edge discriminator for precise timing measurement in the presence of amplitude variations will not lead to optimal results, simply because the time required for the signal to rise from zero to the threshold level will depend on the pulse amplitude and risetime. Several discriminator architectures are available to address this issue. The most widely known is of course the constant fraction discriminator (CFD), which is a leading edge discriminator with a non-constant threshold which looks forward in time, being set ideally to a fixed fraction of the overall pulse height. This is traditionally implemented with a delay line chosen carefully to match the input pulse characteristics. Lumped-element filter circuits can be used as an alternative, however, and are attractive because it is very difficult to integrate a high-quality delay line in a monolithic circuit, especially a modern submicron CMOS process which is intended for digital applications. Several authors have recently reported ASICs incorporating a CFD. Timing resolution of the order of 1 ns FWHM is possible with these monolithic CMOS CFDs. For optimum response, however, it is important to carefully design the delay or filter network to match the characteristics of the input pulse, which could lead to complications.

A second architecture for alleviating time walk effects is the zero-crossing discriminator, which differentiates the input signal and looks for a zero-crossing, which would be associated with the peak of the original signal. The time of this zero-crossing will be independent of the amplitude of the input signal, if everything is linear and there is no slew rate limiting. Recent implementations of zero-crossing discriminators show excellent timing resolution and can be achieved in standard CMOS technology. Both the CFD and the zero-crossing discriminator can still suffer time walk due to non-ideal comparator response (slew rate and overdrive dependence), but at least in the zero-crossing case even this error can be cancelled by clever use of an analog division circuit; performance as good as 0.2 ns FWHM is achievable in standard CMOS.

The third approach to time walk is to use a leading edge discriminator, or some combination of leading edge discriminators, accept that time walk exists in its output, and compensate for it either by sending the comparator output through a variable delay device (analog or digital), or by altering the input signal or threshold, based on the input signal amplitude. In a sense, the standard CFD circuit falls into this category, but there are many other possibilities. The extrapolated leading edge discriminator uses two leading edge discriminators and delays the output of the first one by a constant minus the time difference between the two, to extrapolate back to zero threshold and so zero time walk. Another approach uses a low-resolution flash A/D to control delays applied to either the input or output of a leading edge discriminator. That is rather complex for the present application, however, using a digital delay with direct analog control from the discriminator input signal is a viable alternative.

Many of these discriminators circuits can be used for the LSO/APD readout chip for PET imaging. It is important to select the best architecture, which minimizes circuit area and complexity, power dissipation, sensitivity to process variations, and temperature coefficient, while meeting the required time resolution specification. It is very likely that a compensated leading edge discriminator will provide the most efficient and robust implementation with sufficient performance. Leading edge discriminators 105, 107 have been already used successfully and the results are presented here.

The circuit was tested with a single-pixel APD 121, type RMD S0223, coupled with Bicron BC-630 optical grease to a 2×2×10 mm$^3$ LSO crystal 120 wrapped in reflective white teflon tape (FIG. 11). Except for the number of pixels, the specifications of this APD type exactly match those of the 4×4 pixel array for which the readout ASIC will be developed. The detector was irradiated by a $^{22}$Na positron source. To detect gamma-gamma coincidences from the positron annihilation, we used a second LSO crystal 123 coupled to a ⅜" photomultiplier tube (Hamamatsu R1635) 124. To make the alignment of the radioactive source and the two detectors less critical, this LSO crystal was irradiated through one of its 2×10 mm$^2$ wide faces. The output signals from the APD preamplifier 126, the discriminator 128, and the PMT were recorded on a high-bandwidth, high-sample rate digital storage oscilloscope 127 (Tektronix TDS 7104, bandwidth 1 GHz, sample rate tip to 10 GS/s, depending on the number of traces recorded) and transferred to a desktop computer via a GPIB connection. A typical APD signal(s) is shown in figures FIG. 12 and FIG. 17. The amplitude of this pulse is typical of the 511 keV photopeak. Calibration of the current on the y axis is based on the measured transimpedance of the amplifier circuit. The pulse fits to $e^{-(t-t_0)/\tau_1} - e^{-(t-t_0)/\tau_2}$, with $\tau_1 = 35$ ns and $\tau_1 = 10.6$ ns. The 10%-90% risetime of such a pulse is 10.1 ns. This indicates that a preamplifier bandwidth in the 100 to 150 MHz region is sufficient; beyond this range the wideband noise will be increasing faster than the signal slew rate, and timing resolution will suffer. Note also that with a 10 to 15 ns risetime, if the threshold can be set at 10% or so, there can be no more than 1 to 1.5 ns time walk for a simple leading edge discriminator, for signals reasonably near the photopeak.

Figure 16:
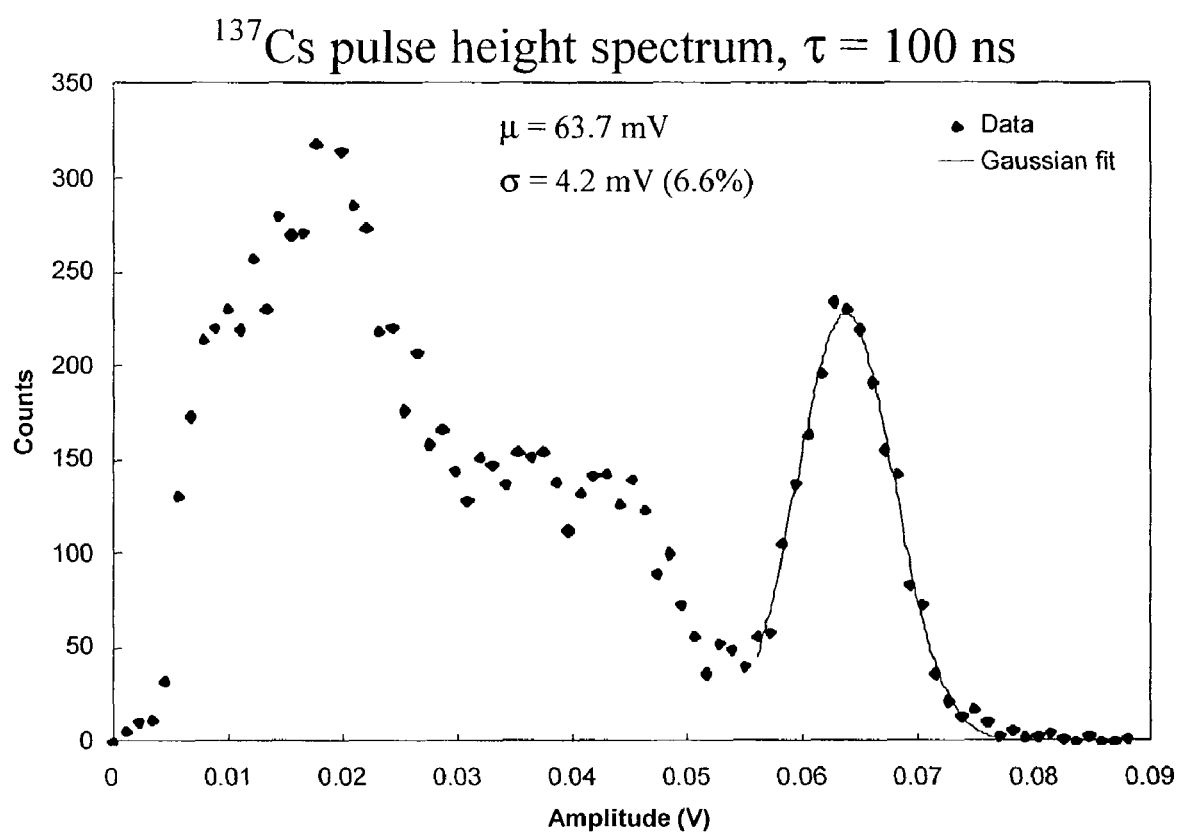
FIG. 16 is a graph of $^{137}$Cs spectrum from LSO scintillator read out by a single-channel APD.
Figure 17:
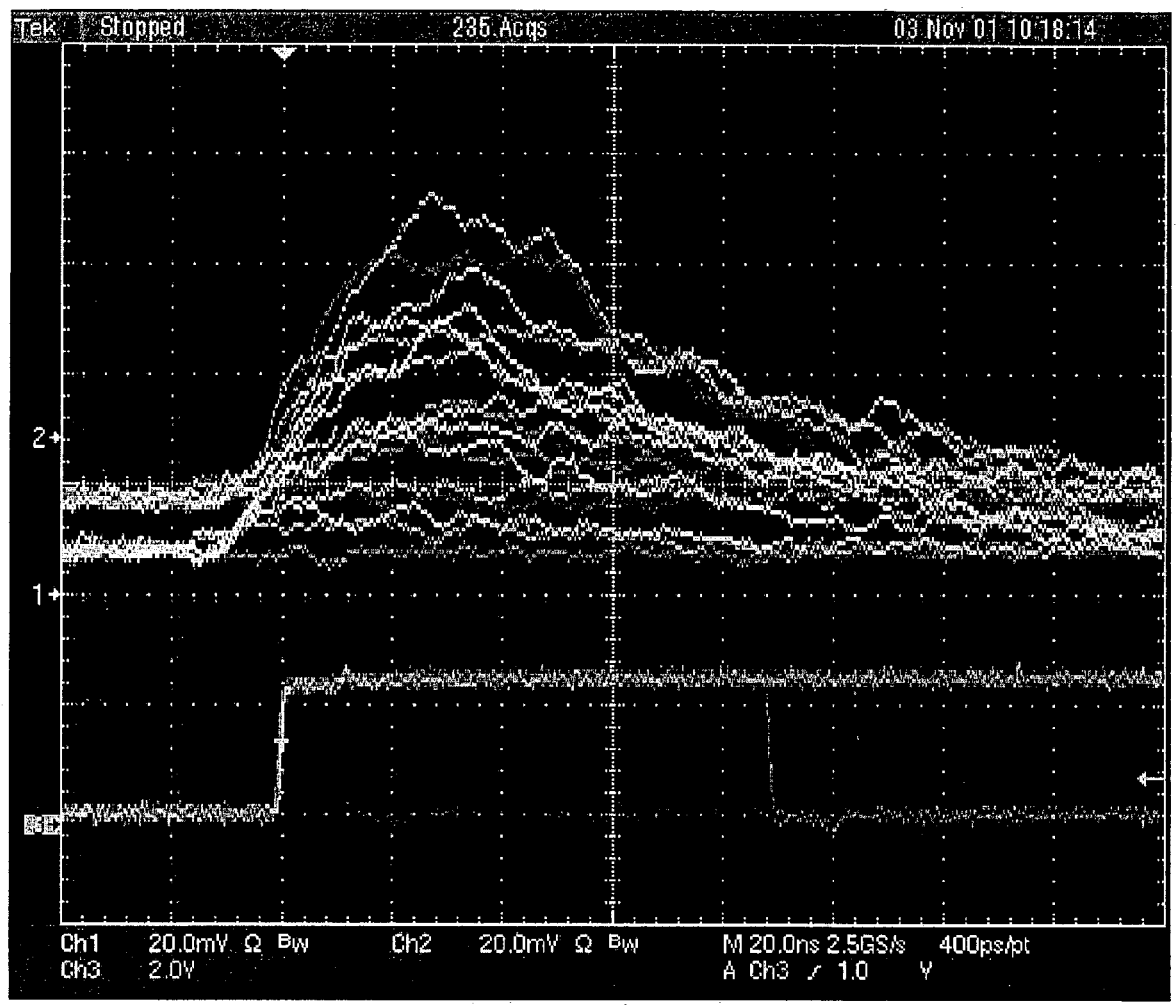
FIG. 17 is an oscilloscope screen plot of typical APD/preamplifier output pulses and also discriminator OR output.

In order to verify the amplitude determination, we acquired data for the 662 keV gamma line from $^{137}$CS. The spectrum is shown in FIG. 16. When compared with sodium data FIG. 15 taken under identical conditions, the two photopeak positions agree to within 3% after correcting for the actual photon energies, less than the width of either peak.

The coincidence time resolution was determined by recording the APD and PMT analog signals in coincidence (with a wide enough coincidence window to avoid affecting the subsequent analysis), setting a threshold safely above the noise level for each of the two signals, and determining the time at which each signal first crossed the threshold. This algorithm simulates a simple leading-edge discriminator. The distribution of time differences between the two signals is plotted in FIG. 13. It has a width of 3.1 ns FWHM; corrections for pulse-height dependent time walk, which have not been applied to the data shown in FIG. 13, reduce this width by only a small amount. This suggests that more complicated discriminator schemes, such as dual-level or constant fraction discriminators may not significantly improve the timing resolution of this circuit. Moreover, the image reconstruction will have to involve a photon energy cut to reduce the background due to gamma scattering in the sample, so those events which are most affected by time walk will not be used for imaging purposes anyway. Therefore, the coincidence window can be adjusted to reflect the (narrower) width of the timing distribution for events that pass the pulse height cut. It should be noted that we did not see any significantly different result when we used the APD discriminator output signal instead of the analog signal to determine the timing. The discriminator worked properly.

The emphasis with prototype circuit B (FIG. 7) is on achieving the required timing and energy resolution under the constraint of low power dissipation. The bandwidth of the preamplifier 63 and the propagation delay of the discriminator (FIG. 8) are both considerably reduced from the levels of prototype circuit A (FIG. 6). As a consequence, circuit B is perhaps less suitable for detailed laboratory studies of the APD current waveform in response to LSO scintillation light. This circuit was a laboratory prototype for the functionality and specifications considered for the ASIC. Of course, the ASIC includes further circuitry besides the preamplifier and discriminator—there will be shapers and sample/hold circuits and an analog output for the pulse height measurement, and there will be some of the coincidence logic and the readout control logic, and there may also be A/D converter(s) and/or Constant fraction discriminators.

Schematic diagrams of prototype circuit B are shown in FIG. 7 and FIG. 8. It is implemented in a bipolar technology, owing to the widespread availability of low noise high speed bipolar transistors for wireless communications. The PET APD readout ASIC may be developed either in bipolar, BiCMOS, or CMOS technology—all should be capable of meeting the specifications, although there will be specific advantages in terms of power efficiency, speed, stability, and cost for these different technologies which will be evaluated. All transistors are Philips BFT25A, chosen for its low noise and for its high $f_T$ (over 3.5 GHz) and β (about 75) at a low (500 μA) DC collector current, which makes it especially suitable for low power, high speed amplifiers. The same parameters are also crucial for a low current noise amplifier, since the current noise at low to medium frequencies is dominated by the base current shot noise, which in this amplifier is a low 1.72 pA/√Hz (the base bias current is 9.26 μA).

The transimpedance amplifier 63 is a two-stage design; the first stage provides an output signal current which is proportional to the APD signal current. In the second stage this current is applied to a load resistor, the resulting voltage is buffered, and then it goes to a further gain stage 65 which has a differential output; in this stage is also a baseline restorer, which also serves for the introduction of an intentional offset voltage 70 to lower the positive output (A+ on the schematic) 71 below the negative output (A−) 71. This offset voltage is the discriminator threshold level—the differential-input, differential-output discriminator, which follows has its nominal threshold at zero volts. A fully DC coupled circuit, replacing the baseline restorer with a suitable bias voltage circuit, would also be possible in the ASIC (and perhaps would be preferred for operation at high count rates), but it was felt that for the discrete component prototype this could not be successfully implemented, owing to device matching problems and temperature differentials on the printed circuit board. This gives another reason for preferring ASIC over a system based on discrete components.

The noise of the transimpedance amplifier 63 of circuit B is significantly lower than that of circuit A 43. Partially this is due to the lower bandwidth, but in addition this circuit is more optimized for the relatively high source capacitance of the APD (and of the interconnect which will be necessary in a realistic multichannel system), compared with the capacitance of a photodiode for fiberoptic data receiver applications. Of course in an ASIC the noise can be reduced further since the parasitic capacitances are smaller and the transistor geometry can be tuned. With 5 pF source capacitance, we measured 25 nA rms (a signal to noise ratio of 160 at typical signal levels). SPICE simulations indicate 33.7 nA rms. The major noise contributions at low to medium frequencies are from the input transistor base shot noise (1.72 pA/√Hz) and the feedback resistor current noise (1.17 pA/√Hz), adding to 2.08 pA/√Hz; at high frequencies the major noise contributions are from the input transistor base resistance and collector shot noise. The effect of the latter is dependent on the source capacitance. In addition to these amplifier noise sources, there is of course the APD noise current, about 3 to 5 pA/√Hz.

The discriminator of prototype circuit B is a low power, reduced signal swing version of traditional differential ECL buffers such as the MC100EL16 used in prototype circuit A. The input signal swing is small, and the common-mode level is precisely controlled; for this reason a more general purpose comparator input stage would be an unnecessary effort. The small signal swing internally and at the output helps to minimize propagation delay dependence on the input signal slew rate and overdrive, and our $^{22}$Na coincidence measurements show that such propagation delay variations are indeed under control.

The transimpedance amplifier 63, 71 outputs and also the discriminator outputs 91 of prototype circuit B are buffered for transmission to the oscilloscope with four AD8009 wideband op-amps in an overall unity gain configuration. The large signal −3 dB bandwidth of these buffers (2 V p-p, greater than our maximum signal swing here) is 440 MHz, so they do not limit our measurements. Similarly, the noise contribution of these buffers to the transimpedance amplifier output signals is around 1.8 nA rms (input referred), so again they are not limiting the measurements. Power dissipation for prototype circuit B is 22.2 mW (measured); as with circuit A this figure is for the indicated circuit only and excludes the test point buffers.

A photograph of the prototype circuit B (FIG. 7 and FIG. 8) is shown in FIG. 9. Note the APD and LSO crystal (wrapped in white tape) installed on the 8-pin DIP header near the upper left.

Performance of the circuit was investigated using the same setup as the one described for circuit A (FIG. 6). The energy resolution and the timing resolution between the APD and PMT were measured. The APD preamplifier signals were filtered with an $RC^2$ filter with a time constant of 50 ns. A sample $^{22}$Na source spectrum obtained with circuit B is shown in FIG. 15. Compared to circuit B results, the width of the photopeak is slightly improved, to 15.8% FWHM. Such an improvement is to be expected from the lower noise level of circuit B.

For an alternative assessment of the energy resolution, we used the oscilloscope's built-in mathematical capabilities to integrate the APD signal over a period of 240 ns, starting 40 ns before the trigger point. The resulting photopeak histogram had a width of 13.6% FWHM.

The timing spectra is acquired with circuit B. Due to the low preamplifier noise, however, it was possible to set the discriminator threshold low enough that signals which were high enough to be relevant for PET imaging were not significantly affected by this time walk. With a pulse height cut corresponding to 350 keV photon energy, a typical value for PET applications, a timing resolution of 1.1 ns FWHM and 2.2 ns full width at one tenth the maximum (FWTM) was obtained. The spectrum shown in FIG. 14 uses a more conservative cut value of 300 keV and yields a resolution of 1.5 ns FWHM, 2.7 ns FWTM.

In designing the readout electronics for an LSO/APD based PET system, the main consideration is to obtain high-resolution coincidence timing. This is required to achieve the combination of high singles count rates and low accidental coincidence rates that is needed for high-contrast PET imaging. Spurious coincidences create an image background by yielding reconstructed photon directions that have no correlation with the actual source distribution. By a rough estimate, we expect a singles rate of about 1.5 million counts/s in a PET system consisting of an 18 cm diameter, 2 cm axial length detector ring (2000 pixels) for a 10 mCi injection. Assuming that these counts are evenly distributed over all pixels and that coincidences are formed between each module and a 120° ring section across from it (for a field of view of half the ring diameter), this leads to an accidental coincidence rate of 750 counts/s, per nanosecond timing resolution. This has to be compared to an estimated true coincidence rate of 10-15 kcounts/s. Work discussed here has demonstrated that a coincidence timing resolution of better than 2 ns FWHM is achievable for coincidences between an APD and a (significantly faster) PMT. By taking coincidences between two APDs instead, the width is expected to increase by no more than 50%. Based on that, and the system requirements outlined above, a design target for the ASIC a coincidence timing resolution<3 ns FWHM measured between two APD channels with a positron annihilation source and 2×2×20 mm$^3$ LSO crystals is set.

To achieve the goal of high-resolution timing, we will continue to focus our chip design efforts on two main areas, the preamplifier and the timing discriminator. As discussed above, a low-noise, fast preamplifier will help improve timing resolution in two ways, by reducing the (noise-induced) amplitude variations that invariably translate into timing fluctuations, and by minimizing (by virtue of a fast signal rise time) the direct slope-induced time walk, for instance in a leading edge level crossing discriminator. Based on the results, a leading edge design may be sufficient for obtaining good timing resolution; this will considerably simplify the ASIC design and help us to keep the chip's power dissipation low.

In order to make a practical large-scale high-resolution coincidence system, it is also necessary to address the issue of controlling signal-independent systematic variations from channel to channel in propagation delay (and therefore also in signal baseline and discriminator threshold, at least with leading edge discrimination). To do so, we will investigate methods to minimize the variations and more importantly their temperature coefficients, and also will implement delay tuning circuitry on a channel-by-channel basis to line up the discriminator outputs in the coincidence logic.

Energy measurement of each pulse is also important, in order to reject the background from scatter within the imaged object or other material. However, only a modest energy resolution is already sufficient for this purpose. As discussed above, the work with this APD has yielded an energy resolution of approximately 15% FWHM at 511 keV, and at most minor changes to this value in the ASIC, due, for example, to further optimization of the shaper parameters or unexpected noise pickup is expected.

For maximum sensitivity, and hence minimum total dose to the patient, at high event rates, it is very important that the front end electronics and readout system impose the minimum practical dead time due to event processing. We will take this into account in the design of the readout circuitry, and expect to meet a deadtime specification of no more than 200 to 300 ns per hit, and furthermore that this deadtime will only apply to the channels which are hit, not to an entire APD module or readout group. Therefore a special pipeline technology can be implemented on the ASIC to keep the readout working while the data is transferred to the data acquisition computer. It is important to achieve fast data rate, therefore, the ASIC is designed to be able to use innovative techniques to achieve this. Other innovative features, besides the pipeline data readout system, are; to have on board ADC circuitry where no analog output is needed from the chip; fast analog circuitry; fast discriminator circuits such as constant fraction discriminator; large gain-bandwidth product; elimination of sample-and-hold by using flash A/D converter combined to the pipeline readout; on board coincidence detection circuit; on board elimination or discrimination of events where only an APD on one end of the LSO crystal detector produces a signal not in coincidence with the APD on the other end; on board DOI determination; a channel to channel time difference measuring system using the signals $V_U2$, 14 and $V_V3$, 15 and a completely digital circuit where the input signals are shaped or without shaping are digitized immediately and time tagged and send outside the chip to a very fast computer for realtime and/or post processing. The chip may also have onboard adjustments for amplifier gains and offsets, and discriminator or comparator thresholds.

In designing the readout modules for the APD arrays, special care will be taken to minimize the amount of inactive material in front of and between the LSO crystals. This will help minimize blurring caused by photon scattering in these materials and maximize the detection efficiency of the system. Obviously, it will not be possible to eliminate all material from the inside of the ring formed by the detector arrays; most notably, the APDs and readout chips required for DOI measurements will have to be right on the inner surface. However, by moving all support circuitry except the most essential bypass capacitors to the outside edge of the ring, will reduce the impact of these components to a minimum.

Another important consideration in designing a PET detector system with a large number of elements is the design of the overall trigger logic. We plan to implement a decentralized system, in which each 16-element or 64-element detector module with ASICs on each end sends its timing discriminator signals onto a bus that is connected to as, many modules on the opposite side of the ring as are needed to achieve the desired field of view. Each module autonomously determines whether there is a coincidence between its own timing signals and any of the signals coming in from across the ring; if this is the case, the module then initiates the readout of its relevant timing and pulse height data. (A valid event then requires that both of the modules involved recognize the coincidence). Compared to a centralized design, this approach considerably simplifies the trigger logic (no need for a complicated coincidence matrix, nor to feed the coincidence outputs back to the affected modules in order to initiate readout), albeit at the slight expense of having to have trigger circuitry on each module. In another embodiment, a processing system external to the detector modules receive all the trigger and/or pulse height and/or DOI information with channel addresses which have a hit and determines which data to read, and/or calculates the gamma ray directions or the event chord and sends processed data to the imaging computer. In another embodiment all these functions are carried out on the ASICs and the processed data goes to the imaging computer. In another embodiment, microprocessors are placed on the side of the ASICs which carry put the processing of the data and the processed data goes to the imaging computer. In another embodiment, chips send out raw digitized data very fast to a fast data acquisition/analysis/imaging computer or computers, which process the raw data and produce an image.

What is claimed:

1. A medical imaging system for imaging at least one portion of at least one living organism, said at least one portion treated with at least one radiopharmaceutical, said at least one radiopharmaceutical emitting a plurality of positrons which annihilate and produce a plurality of photons, comprising:
    at least one detector system comprised of a plurality of position sensitive photon detectors,
    wherein at least one entrance aperture of said at least one detector system is external to said at least one living organism and proximate to said at least one portion of said at least one living organism,
    wherein at least one portion of said plurality of photons pass into at least one portion of said plurality of position sensitive detectors, and
    wherein said plurality of position sensitive photon detectors comprise at least one scintillator with at least one first side connected to at least one first scintillation light detector and at least one second side connected to at least one second scintillation light detector;
    at least one multi-channel integrated circuit coupled to said plurality of position sensitive photon detectors;
    at least one processor coupled to said at least one multi-channel integrated circuit; and
    at least one display system coupled to said at least one processor, said display system displaying at least one image of said at least one portion of said at least one living organism.

2. The medical imaging system of claim 1, wherein a portion of said plurality of photons undergo at least one photoelectric absorption in at least one portion of said plurality of position sensitive photon detectors.

3. The medical imaging system of claim 1, further comprising at least one collimator to restrict at least one of said at least one entrance aperture.

4. The medical imaging system of claim 1, further comprising at least two of said at least one detector system positioned on opposite sides of said at least one portion of said at least one living organism.

5. The medical imaging system of claim 1, further comprising at least two of said at least one detector systems positioned to receive at least one portion of said plurality of photons from said at least one portion of said at least one living organism.

6. The medical imaging system of claim 1, further at least one septa placed in between at least one portion of said plurality of position sensitive photon detectors.

7. The medical imaging system of claim 1, further comprising at least one ring of at least two of said at least one detector system positioned to receive at least one portion of said plurality of photons from said at least one portion of said at least one living organism.

8. The medical imaging system of claim 1, wherein at least one of said at least one multi-channel integrated circuit and said at least one processor determines at least one depth of interaction for at least one portion of said plurality of photons inside at least one portion of said plurality of position sensitive photon detectors.

9. The medical imaging system of claim 1, wherein at least one of said at least one multi-channel integrated circuit and said at least one processor determines a depth of interaction of at least one portion of said plurality of photons inside at least one portion of said plurality of position sensitive photon detectors, wherein said depth of interaction is used to reduce radial elongation error.

10. The medical imaging system of claim 1, wherein at least one of said at least one multi-channel integrated circuit and said at least one processor determines an energy of a portion of said plurality of photons.

11. The medical imaging system of claim 1, wherein at least one of said at least one multi-channel integrated circuit and said at least one processor determines a direction of a portion of said plurality of photons.

12. The medical imaging system of claim 1, wherein at least one of said at least one multi-channel integrated circuit and said at least one processor determines an arrival time of a portion of said plurality of photons.

13. The medical imaging system of claim 1, wherein said at least one multi-channel integrated circuit produces at least one timing signal and at least one position data for a portion of said plurality of photons;
    wherein said at least one processor receives and processes said at least one timing signal and said at least one position data from said at least one multi-channel integrated circuit to produce information; and
    wherein said at least one display system receives said information from said at least one processor to display at least one image of said at least one portion of said at least one living organism.

14. The medical imaging system of claim 1, wherein said at least one portion of said at least one living organism is all of said at least one organism.

15. The medical imaging system of claim 1, wherein a portion of said plurality of photons undergo at least one Compton scatter in at least one portion of said plurality of position sensitive photon detectors.

16. The medical imaging system of claim 1, further comprising at least one septa placed inside at least one portion of said at least one detector system.

17. A method of imaging at least one portion of at least one living organism, comprising:
    treating said at least one portion of said at least one living organism with at least one radiopharmaceutical, wherein said radiopharmaceutical produces a plurality of photons;

providing at least one detection system comprising at least one scintillator and at least two scintillator light detectors;

connecting at least a first scintillator light detector to at least a first side of said at least one scintillator, and at least a second scintillator light detector to at least a second side of said at least one scintillator;

positioning said at least one detection system to receive at least a portion of said plurality of photons;

determining a direction of at least one portion of said plurality of photons entering said detection system;

processing said direction for a portion of said portion of plurality of photons to produce at least one image of said at least one portion of said at least one living organism; and displaying said at least one image of said at least one portion of said at least one living organism.

18. The imaging method of claim 17, wherein displaying said at least one image comprises displaying all of said at least one organism.

19. The imaging method of claim 17, wherein at least one collimator limits said direction of at least one portion of said plurality of photons received.

20. The imaging method of claim 17, wherein at least one septa is used to limit said direction of at least one portion of said plurality of photons received.

21. The imaging method of claim 17, further comprising coupling at least one multi-channel integrated circuit to at least one portion of said at least one detection system.

22. The imaging method of claim 17, further comprising:
producing at least one timing signal and at least one position data for a portion of said plurality of photons; and
processing said at least one timing signal and said at least one position data to produce at least one image of said at least one portion of said at least one living organism.

23. The imaging method of claim 17, further comprising determining a depth of interaction of at least one portion of said plurality of photons inside at least one detection system.

24. The imaging method of claim 23, further comprising reducing a radial elongation error by using said depth of interaction information.

* * * * *